(12) United States Patent
Ocel et al.

(10) Patent No.: US 8,623,010 B2
(45) Date of Patent: Jan. 7, 2014

(54) CARDIAC MAPPING INSTRUMENT WITH SHAPEABLE ELECTRODE

(75) Inventors: Jon M. Ocel, Lino Lakes, MN (US); Roderick E. Briscoe, Rogers, MN (US); David E. Francischelli, Anoka, MN (US); Scott E. Jahns, Hudson, WI (US); James R. Keogh, Maplewood, MN (US); Katherine S. Jolly, Shoreview, MN (US); Matthew D. Bonner, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1247 days.

(21) Appl. No.: 12/480,926

(22) Filed: Jun. 9, 2009

(65) Prior Publication Data

US 2009/0326527 A1 Dec. 31, 2009

Related U.S. Application Data

(60) Division of application No. 10/853,594, filed on May 25, 2004, now abandoned, which is a continuation-in-part of application No. 10/056,807, filed on Jan. 25, 2002, now Pat. No. 7,967,816.

(51) Int. Cl.
*A61B 18/14* (2006.01)

(52) U.S. Cl.
USPC ............................................. 606/41; 607/119

(58) Field of Classification Search
USPC .................. 606/32–35, 38–41; 607/6, 9, 119; 600/547
See application file for complete search history.

(56) References Cited

U.S. PATENT DOCUMENTS

| | | | |
|---|---|---|---|
| 1,735,271 A | 11/1929 | Groff | |
| 3,736,936 A | 6/1973 | Basiulis et al. | |
| 3,807,403 A | 4/1974 | Stumpf et al. | |
| 3,823,575 A | 7/1974 | Parel | |
| 3,823,718 A | 7/1974 | Tromovitch | |
| 3,827,436 A | 8/1974 | Stumpf et al. | |
| 3,830,239 A | 8/1974 | Stumpf | |
| 3,859,986 A | 1/1975 | Okada et al. | |
| 3,862,627 A | 1/1975 | Hans, Sr. | |
| 3,886,945 A | 6/1975 | Stumpf et al. | |

(Continued)

FOREIGN PATENT DOCUMENTS

| | | |
|---|---|---|
| EP | 1095627 | 5/2001 |
| WO | 01/80755 | 11/2001 |

OTHER PUBLICATIONS

Bredikis and Bredikis; Surgery of Tachyarrhythmia: Intracardiac Closed Heart Cryoablation; PACE, vol. 13, pp. 1980-1984.

(Continued)

*Primary Examiner* — Michael Peffley

(57) ABSTRACT

An instrument including an elongated shaft and a non-conductive handle is disclosed. The shaft defines a proximal section and a distal section. The distal section forms an electrically conductive tip. Further, the shaft is adapted to be transitionable from a straight state to a first bent state. The shaft is capable of independently maintaining the distinct shapes associated with the straight state and the first bent state. The handle is rigidly coupled to the proximal section of the shaft. The instrument is useful for epicardial pacing and/or mapping of the heart for temporary pacing on a beating heart, for optimizing the placement of ventricular leads for the treatment of patients with congestive heart failure and ventricular dysynchrony and/or for use in surgical ablation procedures.

11 Claims, 22 Drawing Sheets

(56) References Cited

U.S. PATENT DOCUMENTS

| | | | |
|---|---|---|---|
| 3,907,339 | A | 9/1975 | Stumpf et al. |
| 3,910,277 | A | 10/1975 | Zimmer |
| 3,913,581 | A | 10/1975 | Ritson et al. |
| 3,924,628 | A | 12/1975 | Droegemueller et al. |
| 4,018,227 | A | 4/1977 | Wallach |
| 4,022,215 | A | 5/1977 | Benson |
| 4,061,135 | A | 12/1977 | Widran et al. |
| 4,063,560 | A | 12/1977 | Thomas et al. |
| 4,072,152 | A | 2/1978 | Linehan |
| 4,082,096 | A | 4/1978 | Benson |
| 4,207,897 | A | 6/1980 | Lloyd et al. |
| 4,248,224 | A | 2/1981 | Jones |
| 4,275,734 | A | 6/1981 | Mitchiner |
| 4,278,090 | A | 7/1981 | van Gerven |
| 4,326,529 | A | 4/1982 | Doss et al. |
| 4,377,168 | A | 3/1983 | Rzasa et al. |
| 4,519,389 | A | 5/1985 | Gudkin et al. |
| 4,598,698 | A | 7/1986 | Siegmund |
| 4,601,290 | A | 7/1986 | Effron et al. |
| 4,664,110 | A | 5/1987 | Schanzlin |
| 4,736,749 | A | 4/1988 | Lundback |
| 4,779,611 | A | 10/1988 | Grooters et al. |
| 4,802,475 | A | 2/1989 | Weshahy |
| 4,815,470 | A | 3/1989 | Curtis et al. |
| 4,872,346 | A | 10/1989 | Kelly-Fry et al. |
| 4,916,922 | A | 4/1990 | Mullens |
| 4,917,095 | A | 4/1990 | Fry et al. |
| 4,920,982 | A | 5/1990 | Goldstein |
| 4,936,281 | A | 6/1990 | Stasz |
| 4,946,460 | A | 8/1990 | Merry et al. |
| 5,013,312 | A | 5/1991 | Parins et al. |
| 5,029,574 | A | 7/1991 | Shimamura et al. |
| 5,044,165 | A | 9/1991 | Linner et al. |
| 5,078,713 | A | 1/1992 | Varney |
| 5,080,102 | A | 1/1992 | Dory |
| 5,080,660 | A | 1/1992 | Buelna |
| 5,100,388 | A | 3/1992 | Behl et al. |
| 5,108,390 | A | 4/1992 | Potocky et al. |
| 5,147,355 | A | 9/1992 | Friedman et al. |
| 5,151,102 | A | 9/1992 | Kamiyama et al. |
| 5,156,613 | A | 10/1992 | Sawyer |
| 5,167,659 | A | 12/1992 | Ohtomo et al. |
| 5,178,133 | A | 1/1993 | Pena |
| 5,207,674 | A | 5/1993 | Hamilton |
| 5,217,460 | A | 6/1993 | Knoepfler |
| 5,217,860 | A | 6/1993 | Fahy et al. |
| 5,222,501 | A | 6/1993 | Ideker et al. |
| 5,224,943 | A | 7/1993 | Goddard |
| 5,228,923 | A | 7/1993 | Hed |
| 5,231,995 | A | 8/1993 | Desai |
| 5,232,516 | A | 8/1993 | Hed |
| 5,254,116 | A | 10/1993 | Baust et al. |
| 5,263,493 | A | 11/1993 | Avitall |
| 5,269,291 | A | 12/1993 | Carter |
| 5,275,595 | A | 1/1994 | Dobak, III |
| 5,277,201 | A | 1/1994 | Stern |
| 5,281,213 | A | 1/1994 | Milder et al. |
| 5,281,215 | A | 1/1994 | Milder |
| 5,295,484 | A | 3/1994 | Marcus et al. |
| 5,300,087 | A | 4/1994 | Knoepfler |
| 5,309,896 | A | 5/1994 | Moll et al. |
| 5,314,466 | A | 5/1994 | Stern et al. |
| 5,316,000 | A | 5/1994 | Chapelon et al. |
| 5,317,878 | A | 6/1994 | Bradshaw et al. |
| 5,318,525 | A | 6/1994 | West et al. |
| 5,318,589 | A | 6/1994 | Lichtman |
| 5,322,520 | A | 6/1994 | Milder |
| 5,323,781 | A | 6/1994 | Ideker et al. |
| 5,324,255 | A | 6/1994 | Passafaro et al. |
| 5,324,284 | A | 6/1994 | Imran |
| 5,324,286 | A | 6/1994 | Fowle |
| 5,334,181 | A | 8/1994 | Rubinsky et al. |
| 5,334,193 | A | 8/1994 | Nardella |
| 5,348,554 | A | 9/1994 | Imran et al. |
| 5,353,783 | A | 10/1994 | Nakao et al. |
| 5,354,258 | A | 10/1994 | Dory |
| 5,361,752 | A | 11/1994 | Moll et al. |
| 5,364,394 | A | 11/1994 | Mehl |
| 5,383,874 | A | 1/1995 | Jackson et al. |
| 5,385,148 | A | 1/1995 | Lesh et al. |
| 5,395,312 | A | 3/1995 | Desai |
| 5,395,363 | A | 3/1995 | Billings et al. |
| 5,396,887 | A | 3/1995 | Imran |
| 5,397,304 | A | 3/1995 | Truckai |
| 5,400,770 | A | 3/1995 | Nakao et al. |
| 5,400,783 | A | 3/1995 | Pomeranz et al. |
| 5,401,272 | A | 3/1995 | Perkins |
| 5,403,309 | A | 4/1995 | Coleman et al. |
| 5,403,311 | A | 4/1995 | Abele et al. |
| 5,403,312 | A | 4/1995 | Yates et al. |
| 5,405,376 | A | 4/1995 | Mulier et al. |
| 5,409,483 | A | 4/1995 | Campbell et al. |
| 5,421,819 | A | 6/1995 | Edwards et al. |
| 5,423,807 | A | 6/1995 | Milder |
| 5,423,811 | A | 6/1995 | Imran et al. |
| 5,427,119 | A | 6/1995 | Swartz et al. |
| 5,431,649 | A | 7/1995 | Mulier et al. |
| 5,433,708 | A | 7/1995 | Nichols et al. |
| 5,435,308 | A | 7/1995 | Gallup et al. |
| 5,435,805 | A | 7/1995 | Edwards et al. |
| 5,437,651 | A | 8/1995 | Todd et al. |
| 5,441,499 | A | 8/1995 | Fritzsch |
| 5,443,463 | A | 8/1995 | Stern et al. |
| 5,443,470 | A | 8/1995 | Stern et al. |
| 5,450,843 | A | 9/1995 | Moll et al. |
| 5,452,582 | A | 9/1995 | Longsworth |
| 5,452,733 | A | 9/1995 | Sterman et al. |
| 5,458,596 | A | 10/1995 | Lax et al. |
| 5,458,598 | A | 10/1995 | Feinberg et al. |
| 5,462,545 | A | 10/1995 | Wang et al. |
| 5,465,717 | A | 11/1995 | Imran et al. |
| 5,469,853 | A | 11/1995 | Law et al. |
| 5,470,308 | A | 11/1995 | Edwards et al. |
| 5,470,309 | A | 11/1995 | Edwards et al. |
| 5,472,441 | A | 12/1995 | Edwards et al. |
| 5,472,876 | A | 12/1995 | Fahy |
| 5,478,309 | A | 12/1995 | Sweezer et al. |
| 5,478,330 | A | 12/1995 | Imran et al. |
| 5,484,400 | A | 1/1996 | Edwards et al. |
| 5,486,193 | A | 1/1996 | Bourne et al. |
| 5,487,385 | A | 1/1996 | Avitall |
| 5,487,757 | A | 1/1996 | Truckai et al. |
| 5,496,312 | A | 3/1996 | Klicek |
| 5,497,774 | A | 3/1996 | Swartz et al. |
| 5,498,248 | A | 3/1996 | Milder |
| 5,500,012 | A | 3/1996 | Brucker et al. |
| 5,505,730 | A | 4/1996 | Edwards |
| 5,516,505 | A | 5/1996 | McDow |
| 5,520,682 | A | 5/1996 | Baust et al. |
| 5,522,870 | A | 6/1996 | Ben-Zion |
| 5,536,267 | A | 7/1996 | Edwards et al. |
| 5,542,915 | A | 8/1996 | Edwards et al. |
| 5,545,171 | A | 8/1996 | Sharkey et al. |
| 5,545,195 | A | 8/1996 | Lennox et al. |
| 5,545,200 | A | 8/1996 | West et al. |
| 5,546,940 | A * | 8/1996 | Panescu et al. ............... 600/374 |
| 5,549,661 | A | 8/1996 | Kordis et al. |
| 5,554,110 | A | 9/1996 | Edwards et al. |
| 5,555,883 | A | 9/1996 | Avitall |
| 5,556,377 | A | 9/1996 | Rosen et al. |
| 5,558,671 | A | 9/1996 | Yates |
| 5,558,673 | A | 9/1996 | Edwards et al. |
| 5,560,362 | A | 10/1996 | Sliwa, Jr. et al. |
| 5,562,720 | A | 10/1996 | Stern et al. |
| 5,569,241 | A | 10/1996 | Edwards |
| 5,569,242 | A | 10/1996 | Lax et al. |
| 5,571,088 | A | 11/1996 | Lennox et al. |
| 5,571,215 | A | 11/1996 | Sterman et al. |
| 5,573,532 | A | 11/1996 | Chang et al. |
| 5,575,766 | A | 11/1996 | Swartz et al. |
| 5,575,788 | A | 11/1996 | Baker et al. |
| 5,575,810 | A | 11/1996 | Swanson et al. |
| 5,578,007 | A | 11/1996 | Imran |
| 5,582,589 | A | 12/1996 | Edwards et al. |

(56) References Cited

U.S. PATENT DOCUMENTS

| | | | |
|---|---|---|---|
| 5,582,609 A | 12/1996 | Swanson et al. |
| 5,584,872 A | 12/1996 | LaFontaine et al. |
| 5,588,432 A | 12/1996 | Crowley |
| 5,588,960 A | 12/1996 | Edwards et al. |
| 5,590,657 A | 1/1997 | Cain et al. |
| 5,591,125 A | 1/1997 | Edwards et al. |
| 5,595,183 A | 1/1997 | Swanson et al. |
| 5,599,294 A | 2/1997 | Edwards et al. |
| 5,599,295 A | 2/1997 | Rosen et al. |
| 5,607,389 A | 3/1997 | Edwards et al. |
| 5,607,462 A | 3/1997 | Imran |
| 5,609,151 A | 3/1997 | Mulier et al. |
| 5,617,854 A | 4/1997 | Munsif |
| 5,630,794 A | 5/1997 | Lax et al. |
| 5,630,837 A | 5/1997 | Crowley |
| 5,637,090 A * | 6/1997 | McGee et al. ............... 600/374 |
| 5,643,197 A | 7/1997 | Brucker et al. |
| 5,647,871 A | 7/1997 | Levine et al. |
| 5,656,029 A | 8/1997 | Imran et al. |
| 5,658,278 A | 8/1997 | Imran et al. |
| 5,667,488 A | 9/1997 | Lundquist et al. |
| 5,671,747 A | 9/1997 | Connor |
| 5,672,153 A | 9/1997 | Lax et al. |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |
| 5,681,277 A | 10/1997 | Edwards et al. |
| 5,681,278 A | 10/1997 | Igo et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,713,942 A | 2/1998 | Stern et al. |
| 5,716,389 A | 2/1998 | Walinsky et al. |
| 5,718,241 A | 2/1998 | Ben-Haim et al. |
| 5,718,701 A | 2/1998 | Shai et al. |
| 5,720,718 A | 2/1998 | Rosen et al. |
| 5,720,775 A | 2/1998 | Larnard |
| 5,722,402 A | 3/1998 | Swanson et al. |
| 5,725,524 A | 3/1998 | Mulier et al. |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,735,280 A | 4/1998 | Sherman et al. |
| 5,735,290 A | 4/1998 | Sterman et al. |
| 5,749,846 A | 5/1998 | Edwards et al. |
| 5,755,760 A | 5/1998 | Maguire et al. |
| 5,769,846 A | 6/1998 | Edwards et al. |
| 5,782,828 A | 7/1998 | Chen et al. |
| 5,785,706 A | 7/1998 | Bednarek |
| 5,788,636 A | 8/1998 | Curley |
| 5,792,140 A | 8/1998 | Tu et al. |
| 5,797,960 A | 8/1998 | Stevens et al. |
| 5,800,428 A | 9/1998 | Nelson et al. |
| 5,800,482 A | 9/1998 | Pomeranz et al. |
| 5,810,802 A | 9/1998 | Panescu et al. |
| 5,827,216 A | 10/1998 | Igo et al. |
| 5,827,271 A | 10/1998 | Buysse et al. |
| 5,836,947 A | 11/1998 | Fleischman et al. |
| 5,840,030 A | 11/1998 | Ferek-Petric et al. |
| 5,844,349 A | 12/1998 | Oakley et al. |
| 5,846,187 A | 12/1998 | Wells et al. |
| 5,846,191 A | 12/1998 | Wells et al. |
| 5,849,011 A | 12/1998 | Jones et al. |
| 5,849,028 A | 12/1998 | Chen |
| 5,871,481 A | 2/1999 | Kannenberg et al. |
| 5,871,523 A | 2/1999 | Fleischman et al. |
| 5,871,525 A | 2/1999 | Edwards et al. |
| 5,873,845 A | 2/1999 | Cline et al. |
| 5,873,877 A | 2/1999 | McGaffigan et al. |
| 5,876,399 A | 3/1999 | Chia et al. |
| 5,879,295 A | 3/1999 | Li et al. |
| 5,879,296 A | 3/1999 | Ockuly et al. |
| 5,881,732 A | 3/1999 | Sung et al. |
| 5,882,346 A | 3/1999 | Pomeranz et al. |
| 5,885,278 A | 3/1999 | Fleischman |
| 5,893,848 A | 4/1999 | Negus et al. |
| 5,895,417 A | 4/1999 | Pomeranz et al. |
| 5,897,553 A | 4/1999 | Mulier et al. |
| 5,897,554 A | 4/1999 | Chia et al. |
| 5,899,898 A | 5/1999 | Arless et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,927,284 A | 7/1999 | Borst et al. |
| 5,928,191 A | 7/1999 | Houser et al. |
| 5,931,810 A | 8/1999 | Grabek |
| 5,931,848 A | 8/1999 | Saadat |
| 5,951,546 A | 9/1999 | Lorentzen |
| 5,954,661 A | 9/1999 | Greenspon et al. |
| 5,957,922 A | 9/1999 | Imran |
| 5,964,727 A | 10/1999 | Edwards et al. |
| 5,964,755 A | 10/1999 | Edwards |
| 5,971,980 A | 10/1999 | Sherman |
| 5,971,983 A | 10/1999 | Lesh |
| 5,993,447 A | 11/1999 | Blewett et al. |
| 6,007,499 A | 12/1999 | Martin et al. |
| 6,012,457 A | 1/2000 | Lesh |
| 6,016,811 A | 1/2000 | Knopp et al. |
| 6,022,334 A | 2/2000 | Edwards et al. |
| 6,042,556 A | 3/2000 | Beach et al. |
| 6,053,172 A | 4/2000 | Hovda et al. |
| 6,056,745 A | 5/2000 | Panescu et al. |
| 6,063,081 A | 5/2000 | Mulier |
| 6,071,279 A | 6/2000 | Whayne et al. |
| 6,088,614 A * | 7/2000 | Swanson ............... 600/510 |
| 6,088,894 A | 7/2000 | Oakley |
| 6,096,037 A | 8/2000 | Mulier et al. |
| 6,102,886 A | 8/2000 | Lundquist et al. |
| 6,113,592 A | 9/2000 | Taylor |
| 6,117,101 A | 9/2000 | Diederich et al. |
| 6,120,496 A | 9/2000 | Whayne et al. |
| 6,129,726 A | 10/2000 | Edwards et al. |
| 6,142,993 A | 11/2000 | Whayne et al. |
| 6,142,994 A | 11/2000 | Swanson et al. |
| 6,152,920 A | 11/2000 | Thompson et al. |
| 6,161,543 A | 12/2000 | Cox et al. |
| 6,165,174 A * | 12/2000 | Jacobs et al. ............... 606/41 |
| 6,193,714 B1 | 2/2001 | McGaffigan et al. |
| 6,206,847 B1 | 3/2001 | Edwards et al. |
| 6,217,528 B1 | 4/2001 | Koblish et al. |
| 6,217,576 B1 | 4/2001 | Tu et al. |
| 6,224,592 B1 | 5/2001 | Eggers et al. |
| 6,231,518 B1 | 5/2001 | Grabek et al. |
| 6,235,024 B1 | 5/2001 | Tu |
| 6,237,605 B1 | 5/2001 | Vaska et al. |
| 6,238,347 B1 | 5/2001 | Nix et al. |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,128 B1 | 6/2001 | Knopp et al. |
| 6,270,471 B1 | 8/2001 | Hechel et al. |
| 6,293,943 B1 | 9/2001 | Panescu et al. |
| 6,296,619 B1 | 10/2001 | Brisken et al. |

(56) References Cited

U.S. PATENT DOCUMENTS

| | | | |
|---|---|---|---|
| 6,296,639 B1 | 10/2001 | Truckai et al. | |
| 6,302,880 B1 | 10/2001 | Schaer | |
| 6,311,692 B1 | 11/2001 | Vaska et al. | |
| 6,312,383 B1 | 11/2001 | Lizzi et al. | |
| 6,314,962 B1 | 11/2001 | Vaska et al. | |
| 6,314,963 B1 | 11/2001 | Vaska et al. | |
| 6,325,797 B1 | 12/2001 | Stewart et al. | |
| 6,328,688 B1 | 12/2001 | Borst et al. | |
| 6,328,736 B1 | 12/2001 | Mulier | |
| 6,332,881 B1 | 12/2001 | Carner et al. | |
| 6,358,248 B1 | 3/2002 | Mulier et al. | |
| 6,361,531 B1 | 3/2002 | Hissong | |
| 6,364,876 B1 | 4/2002 | Erb et al. | |
| 6,368,275 B1 | 4/2002 | Sliwa et al. | |
| 6,371,955 B1 | 4/2002 | Fuimaono et al. | |
| 6,383,151 B1 | 5/2002 | Diederich et al. | |
| 6,385,472 B1 | 5/2002 | Hall et al. | |
| 6,391,024 B1 * | 5/2002 | Sun et al. | 606/34 |
| 6,395,038 B1 | 5/2002 | Schroeppel | |
| 6,398,792 B1 | 6/2002 | O'Connor | |
| 6,405,078 B1 | 6/2002 | Moaddeb et al. | |
| 6,409,722 B1 | 6/2002 | Hoey | |
| 6,413,254 B1 | 7/2002 | Hissong et al. | |
| 6,419,648 B1 | 7/2002 | Vitek et al. | |
| 6,419,653 B2 | 7/2002 | Edwards et al. | |
| 6,425,867 B1 | 7/2002 | Vaezy et al. | |
| 6,430,426 B2 | 8/2002 | Avitall | |
| 6,440,130 B1 | 8/2002 | Mulier | |
| 6,443,952 B1 | 9/2002 | Mulier et al. | |
| 6,447,507 B1 | 9/2002 | Bednarek et al. | |
| 6,451,014 B1 | 9/2002 | Wakikaido et al. | |
| 6,461,314 B1 | 10/2002 | Pant et al. | |
| 6,461,356 B1 | 10/2002 | Patterson | |
| 6,464,661 B2 | 10/2002 | Edwards et al. | |
| 6,464,700 B1 | 10/2002 | Koblish et al. | |
| 6,471,697 B1 | 10/2002 | Lesh | |
| 6,471,698 B1 | 10/2002 | Edwards et al. | |
| 6,474,340 B1 | 11/2002 | Vaska et al. | |
| 6,475,216 B2 | 11/2002 | Mulier et al. | |
| 6,477,396 B1 | 11/2002 | Mest et al. | |
| 6,484,727 B1 | 11/2002 | Vaska et al. | |
| 6,488,680 B1 | 12/2002 | Francischelli | |
| 6,502,575 B1 | 1/2003 | Jacobs et al. | |
| 6,514,250 B1 | 2/2003 | Jahns | |
| 6,520,927 B1 | 2/2003 | Unsworth | |
| 6,522,930 B1 | 2/2003 | Schaer et al. | |
| 6,527,767 B2 | 3/2003 | Wang et al. | |
| 6,537,248 B2 | 3/2003 | Mulier | |
| 6,537,272 B2 | 3/2003 | Christopherson et al. | |
| 6,551,300 B1 | 4/2003 | McGaffigan | |
| 6,558,382 B2 | 5/2003 | Jahns | |
| 5,697,536 C1 | 6/2003 | Eggers et al. | |
| 6,584,360 B2 | 6/2003 | Francischelli | |
| 6,585,732 B2 | 7/2003 | Mulier | |
| 6,605,084 B2 | 8/2003 | Acker et al. | |
| 6,607,529 B1 | 8/2003 | Jones et al. | |
| 6,610,054 B1 | 8/2003 | Edwards et al. | |
| 6,610,055 B1 | 8/2003 | Swanson et al. | |
| 6,610,060 B2 | 8/2003 | Mulier | |
| 6,613,048 B2 | 9/2003 | Mulier | |
| 6,645,199 B1 | 11/2003 | Jenkins et al. | |
| 6,648,883 B2 | 11/2003 | Francischelli | |
| 6,656,175 B2 | 12/2003 | Francischelli | |
| 6,663,626 B2 | 12/2003 | Truckai et al. | |
| 6,663,627 B2 | 12/2003 | Francischelli | |
| 6,692,450 B1 | 2/2004 | Coleman | |
| 6,699,240 B2 | 3/2004 | Francischelli | |
| 6,702,811 B2 | 3/2004 | Stewart et al. | |
| 6,706,038 B2 | 3/2004 | Francischelli | |
| 6,706,039 B2 | 3/2004 | Mulier | |
| 6,716,211 B2 | 4/2004 | Mulier | |
| 6,730,079 B2 | 5/2004 | Lovewell | |
| 6,736,810 B2 | 5/2004 | Hoey | |
| 6,755,827 B2 | 6/2004 | Mulier | |
| 6,764,487 B2 | 7/2004 | Mulier | |
| 6,773,433 B2 | 8/2004 | Stewart et al. | |
| 6,776,780 B2 | 8/2004 | Mulier | |
| 6,802,840 B2 | 10/2004 | Chin et al. | |
| 6,807,968 B2 | 10/2004 | Francischelli | |
| 6,814,712 B1 | 11/2004 | Edwards et al. | |
| 6,827,715 B2 * | 12/2004 | Francischelli et al. | 606/34 |
| 6,849,073 B2 | 2/2005 | Hoey | |
| 6,852,091 B2 | 2/2005 | Edwards et al. | |
| 6,855,141 B2 | 2/2005 | Lovewell | |
| 6,858,028 B2 | 2/2005 | Mulier | |
| 6,887,238 B2 | 5/2005 | Jahns | |
| 6,899,711 B2 | 5/2005 | Stewart et al. | |
| 6,911,019 B2 | 6/2005 | Mulier | |
| 6,916,318 B2 | 7/2005 | Francischelli | |
| 6,949,097 B2 | 9/2005 | Stewart et al. | |
| 6,949,098 B2 | 9/2005 | Mulier | |
| 6,960,205 B2 | 11/2005 | Jahns | |
| 6,962,589 B2 | 11/2005 | Mulier | |
| 7,029,470 B2 * | 4/2006 | Francischelli et al. | 606/34 |
| 7,113,831 B2 * | 9/2006 | Hooven | 607/101 |
| 7,192,427 B2 * | 3/2007 | Chapelon et al. | 606/33 |
| 7,201,731 B1 | 4/2007 | Lundquist et al. | |
| 2002/0087157 A1 * | 7/2002 | Sliwa et al. | 606/41 |
| 2003/0045872 A1 | 3/2003 | Jacobs | |
| 2003/0191462 A1 | 10/2003 | Jacobs | |
| 2004/0044340 A1 | 3/2004 | Francischelli | |
| 2004/0082948 A1 | 4/2004 | Stewart et al. | |
| 2004/0092926 A1 | 5/2004 | Hoey | |
| 2004/0138656 A1 | 7/2004 | Francischelli | |
| 2004/0143260 A1 | 7/2004 | Francischelli | |
| 2004/0186465 A1 | 9/2004 | Francischelli | |
| 2004/0215183 A1 | 10/2004 | Hoey | |
| 2004/0220560 A1 | 11/2004 | Briscoe | |
| 2004/0236322 A1 | 11/2004 | Mulier | |
| 2005/0010095 A1 | 1/2005 | Stewart et al. | |
| 2005/0010203 A1 | 1/2005 | Edwards et al. | |
| 2005/0084804 A1 | 4/2005 | Truskett et al. | |
| 2005/0143729 A1 | 6/2005 | Francischelli | |
| 2005/0222562 A1 | 10/2005 | Lovewell | |

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

Gallagher et al., "Cryosurgical Ablation of Accessory Atrioventrical Connections: A Method for Correction of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Techique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.

Cox et al., Surgery for Atrial Fibrillation; Seminars in Thoracic and Cardiovascular Surgery, vol. 1, No. 1 (Jul. 1989) pp. 67-73.

McCarthy et al., "Combined Treatment of Mitral Regurgitation and Atrial Fibrillation with ValvukTlasty and the Maze Procedure," The American Journal of Cardiology 71: 483-486, 1993.

(56) References Cited

OTHER PUBLICATIONS

Yamauchi et al. "Use of Intraoperative Mapping to Optimize Surgical Ablation of Atrial Flutter," The Annals of Thoracic Surgery 56: 337-342, 1993.
Graffigna et al., "Surgical Treatment of Wolff-Parkinson-White Syndrome: Epicardial Approach Without the Use of Cardiopulmonary Bypass," Journal of Cardiac Surgery 8: 108-116, 1993.
Siefert et al., "Radiofrequency Maze Ablation for Atrial Fibrillation," Circulation 90(4): 1-594.
Surgical treatment of atrial fibrillation: a review; Europace (2004) 5, S20-S29.
Elvan et al., "Radiofrequency Catheter Ablation of the Atria Reduces Inducibility and Duration of Atrial Fibrillation in Dog," Circulation 91: 2235-2244, 1995.
Cox et al., "Modification of the Maze Procedure for Atrial Flutter and Atrial Fibrillation, I. Rational and Surgical Results," The Journal of Thoracic Cardiovascular Surgery 110: 473-484, 1995.
Cox, "The Maze III Procedure for Treatment of Atrial Fibrillation," Sabiston DC, ed Atlas of Cardiothoracic Surgery, Philadelphia: WB Saunders: 460-475, 1994.
Sueda et al., "Simple Left Atrial Procedure for Chronic Atrial Fibrillation Associated with Mitral Valve Disease," The Annals of Thoracic Surgery 62(6): 1796-1800, 1996.
Tsui et al., "Maze 3 for Atrial Fibrillation: Two Cuts Too Few?" PACE 17: 2163-2166, 1994.
Kosakai et al., "Cox Maze Procedure for Chronic Atrial Fibrillation Associated with Mitral Valve Disease," The Journal of Thoracic Cardiovascular Surgery 108: 1049-1055, 1994.
Cox et al., "The Surgical Treatment of Atrial Fibrillation, IV Surgical Technique," *J of Thorac Cardiovasc Surg*, 1991: 101: 584-593.
Nardella, "Radio Frequency Energy and Impedance Feedback," SPIE vol. 1068, Catheter Based Sensing and Imaging Technology (1989).
Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.
Sie et al., "Radiofrequency Ablation of Atrial Fibrillation in Patients Undergoing Mitral Valve Surgery. First Experience," Circulation (Nov. 1996) 96:450,I-675,#3946.
Sie et al., "Radiofrequency Ablation of Atrial Fibrillation in Patients Undergoing Valve Surgery," Circulation (Nov. 1997) 84:I450,#2519.
Jais et al., "Catheter Ablation for Paroxysmal Atrial Fibrillation: High Success Rates with Ablation in the Left Atrium," Circulation (Nov. 1996) 94:I-675,#3946.
Cox, "Evolving Applications of the Maze Procedure for Atrial Fibrillation," Ann Thorac Surg, 1993;55:578-580.
Cox et al. "Five-Year Experience with the Maze Procedure for Atrial Fibrillation," Ann Thorac Surg, 1993; 56:814-824.
Avitall et al., "New Monitoring Criteria for Transmural Ablation of Atrial Tissues," Circulation, 1996:94(Supp 1):I-493, #2889.
Cox et al., "An 8 1/2 Year Clinical Experience with Surgery for Atrial Fibrillation," Annals of Surgery, 1996;224(3):267-275.
Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.
Haissaguerre et al., "Right and Left Atrial Radiofrequency Catheter Therapy of Paroxysmal Atrial Fibrillation," Journal of Cardiovascular Electrophysiology, 1996;7(12):1132-1144.
Haissaguerre et al., "Role of Catheter Ablation for Atrial Fibrillation," Current Opinion in Cardiology, 1997;12:18-23.
Kawaguchi et al., "Risks and Benefits of Combined Maze Procedure for Atrial Fibrillation Associated with Organic Heart Disease," JACC, 1996;28(4):985-990.
Cox, et al., "Perinodal cryosurgery for atrioventricular node reentry tachycardia in 23 patients," Journal of Thoracic and Cardiovascular Surgery, 99:3, Mar. 1990, pp. 440-450.
Cox, "Anatomic-Electrophysiologic Basis for the Surgical Treatment of Refractory Ischernic Ventricular Tachycardia," Annals of Surgery, Aug. 1983; 198:2;119-129.
Williams, et al., "Left atrial isolation," J Thorac Cardiovasc Surg; 1980; 80: 373-380.
Scheinman, "Catheter-based Techniques for Cure of Cardiac Arrhythmias," Advances in Cardiovascular Medicine, 1996, ISSN 1075-5527, pp. 93-100.
Sueda et al., "Efficacy of a Simple Left Atrial Procedure for Chronic Atrial Fibrillation in Mitral Valve Operations," Ann Thorac Surg, 1997;63:1070-1075.
J. Thorac Cardiovasc Surg 1991; 101: 402-5—The Surgical Treatment of atriall fibrillation (Summary of the current concepts of the mechanisms of atrial flutter and atrial fibrillation) by James L. Cox, MD; Richard B. Schuessler, PHD; and John P. Boineau, MD.
J. Thorac Cardiovasc Surg 1991; 101: 584-92—The surgical treatment of atrial fibrillation Surgical Technique) by James L. Cox, MD.
Ann Thorac Surg 1996; 62: 1796-800 / Simple Left Atrial Procedure for Chronic Atrial Fibrillation Associated With Mitral Valve Disease by Taijiro Sueda, MD; Hideyuki Nagata, MD; Hiroo Shikata, MD; Kazumasa Orihashi, MD; Satoru Morita, MD; Masafumi Sueshiro, MD; Kenji. Okada, MD and Yuichiro Matsuura, MD.
Pace vol. 15 (Supplement Sep. 1992) pp. 1368-1373 / Transcoronary Chemical Ablation of Arrhythmias by Paul Nellens; Sinan Gursoy; Erik Andries and Pedro Brugada.
European Heart Journal, vol. 12, 1991, pp. 1234-1237 / Chemical ablation by subendocardial injection of ethanol via catheter—preliminary results in the pig heart by P. Weismuller; U. Mayer; P. Richter; F Heieck; M. Kochs and V. Hombach.

\* cited by examiner

CARDIAC MAPPING INSTRUMENT WITH SHAPEABLE ELECTRODE

CROSS-REFERENCE TO RELATED APPLICATIONS

This application is a divisional of U.S. Ser. No. 10/853,594, filed on May 25, 2004, now abandoned, which is a continuation-in-part of U.S. Ser. No. 10/056,807 filed Jan. 25, 2002, issued as U.S. Pat. No. 7,967,816 on Jun. 28, 2011, the disclosures of which are incorporated herein by reference.

FIELD OF THE INVENTION

This invention relates to methods and systems for epicardial pacing and mapping of the heart for temporary pacing on a beating heart, for optimizing the placement of ventricular leads for the treatment of patients with congestive heart failure and ventricular dyssynchrony or for use in surgical ablation procedures. More particularly, it relates to a mapping instrument designed to be indifferent to rotational orientation and including a bendable shaft capable of independently maintaining a desired shape.

BACKGROUND OF THE INVENTION

The heart includes a number of pathways that are responsible for the propagation of signals necessary to produce continuous, synchronized contractions. Each contraction cycle begins in the right atrium where a sinoatrial node initiates an electrical impulse. This impulse then spreads across the right atrium to the left atrium, stimulating the atria to contract. The chain reaction continues from the atria to the ventricles by passing through a pathway known as the atrioventricular (AV) node or junction, which acts as an electrical gateway to the ventricles. The AV junction delivers the signal to the ventricles while also slowing it, so the atria can relax before the ventricles contract.

Disturbances in the heart's electrical system may lead to various rhythmic problems that can cause the heart to beat irregularly, too fast or too slow. Irregular heart beats, or arrhythmia, are caused by physiological or pathological disturbances in the discharge of electrical impulses from the sinoatrial node, in the transmission of the signal through the heart tissue, or spontaneous, unexpected electrical signals generated within the heart. One type of arrhythmia is tachycardia, which is an abnormal rapidity of heart action. There are several different forms of atrial tachycardia, including atrial fibrillation and atrial flutter. With atrial fibrillation, instead of a single beat, numerous electrical impulses are generated by depolarizing tissue at one or more locations in the atria (or possibly other locations). These unexpected electrical impulses produce irregular, often rapid heartbeats in the atrial muscles and ventricles. Patients experiencing atrial fibrillation may suffer from fatigue, activity intolerance, dizziness and even strokes.

The precise cause of atrial fibrillation, and in particular the depolarizing tissue causing "extra" electrical signals, is currently unknown. As to the location of the depolarizing tissue, it is generally agreed that the undesired electrical impulses often originate in the left atrial region of the heart. Recent studies have expanded upon this general understanding, suggesting that nearly 90% of these "focal triggers" or electrical impulses are generated in one (or more) of the four pulmonary veins (PV) extending from the left atrium. In this regard, as the heart develops from an embryotic stage, left atrium tissue may grow or extend a short distance into one or more of the PVs. It has been postulated that this tissue may spontaneously depolarize, resulting in an unexpected electrical impulse(s) propagating into the left atrium and along the various electrical pathways of the heart.

A variety of different atrial fibrillation treatment techniques are available, including drugs, surgery, implants, and ablation. While drugs may be the treatment of choice for some patients, drugs typically only mask the symptoms and do not cure the underlying cause. Implantable devices, on the other hand, usually correct an arrhythmia only after it occurs. Surgical and ablation treatments, in contrast, can actually cure the problem by removing and/or ablating the abnormal tissue or accessory pathway responsible for the atrial fibrillation. The ablation treatments rely on the application of various destructive energy sources to the target tissue, including direct current electrical energy, radiofrequency electrical energy, laser energy, microwave energy, ultrasound energy, thermal energy, and the like. The energy source, such as an ablating electrode, is normally disposed along a distal portion of a catheter or instrument. Ablation of the abnormal tissue or accessory pathway responsible for atrial fibrillation has proven highly viable.

Regardless of the application, ablation of tissue is generally achieved by applying the destructive energy source to the target tissue. For some treatments, an ablating element can be formed as a part of a catheter that is delivered via the vascular system to the target site. While relatively non-invasive, catheter-based treatments present certain obstacles to achieving precisely located, complete ablation lesion patterns due to the highly flexible nature of the catheter itself, the confines of the surgical site, etc.

A highly viable alternative device is the hand-held electrosurgical instrument. As used herein, the term "electrosurgical instrument" includes a hand-held instrument capable of ablating tissue or cauterizing tissue, but does not include a catheter-based device. The instrument is relatively short (as compared to a catheter-based device), and rigidly couples the electrode tip to the instrument's handle that is otherwise held and manipulated by the surgeon. The rigid construction of the electrosurgical instrument requires direct, open access to the targeted tissue. Thus, for treatment of atrial fibrillation via an electrosurgical instrument, it is desirable to gain access to the patient's heart through one or more openings in the patient's chest (such as a sternotomy, a thoracotomy, a small incision and/or a port). In addition, the patient's heart may be opened through one or more incisions, thereby allowing access to the endocardial surface of the heart.

Once the target site (e.g., right atrium, left atrium, epicardial surface, endocardial surface, etc.) is accessible, the surgeon positions the electrode tip of the electrosurgical instrument at the target site. The tip is then energized, ablating (or for some applications, cauterizing) the contacted tissue. A desired lesion pattern is then created (e.g., portions of a known "Maze" procedure) by moving the tip in a desired fashion along the target site. In this regard, the surgeon can easily control positioning and movement of the tip, as the electrosurgical instrument is rigidly constructed and relatively short (in contrast to a catheter-based ablation technique).

Ablation of PV tissue may cause the PV to shrink or constrict due to the relatively small thickness of tissue formed within a PV. Because PVs have a relatively small diameter, a stenosis may result due to the ablation procedure. Even further, other vital bodily structures are directly adjacent each PV. These structures may be undesirably damaged when ablating within a PV. Therefore, a technique has been suggested whereby a continuous ablation lesion pattern is formed in the left atrium wall about the ostium associated with the PV in question. In other words, the PV is electrically isolated from the left atrium by forming an ablation lesion pattern that surrounds the PV ostium. As a result, any undesired electrical impulse generated within the PV would not propagate into the left atrium, thereby eliminating unexpected atria contraction.

Electrosurgical instruments, especially those used for the treatment of atrial fibrillation, have evolved to include additional features that provide improved results for particular procedures. For example, U.S. Pat. No. 5,897,553, the teachings of which are incorporated herein by reference, describes a fluid-assisted electrosurgical instrument that delivers a conductive solution to the target site in conjunction with electrical energy, thereby creating a "virtual" electrode. The virtual electrode technique has proven highly effective in achieving desired ablation while minimizing collateral tissue damage. Other electrosurgical instrument advancements have likewise optimized system performance. However, a common characteristic associated with available electrosurgical instruments is a "designed-in" directional orientation. That is to say, electrosurgical devices, and especially those used for atrial fibrillation treatment procedures, are curved along a length thereof, as exemplified by the electrosurgical instrument of U.S. Pat. No. 5,897,553. In theory, this permanent curved feature facilitates the particular procedure (or lesion pattern) for which the electrosurgical instrument is intended. Unfortunately, however, the actual lesion pattern formation technique and/or bodily structure may vary from what is expected, so that the curve is less than optimal. Additionally, the pre-made curve may be well suited for one portion of a particular procedure (e.g., right atrium ablation pattern during the Maze procedure), but entirely inapplicable to another portion (e.g., left atrium ablation during the Maze procedure). As a result, the electrosurgical instrument design may actually impede convenient use by a surgeon.

Electrosurgical instruments continue to be highly useful for performing a variety of surgical procedures, including surgical treatment of atrial fibrillation. While certain advancements have improved overall performance, the accepted practice of imparting a permanent curve or other shape variation into the instrument itself may impede optimal usage during a particular procedure. Therefore, a need exists for an electrosurgical instrument that, as initially presented to a surgeon, is indifferent to rotational orientation, and further is capable of independently maintaining a number of different shapes as desired by the surgeon.

In cases of atrial fibrillation, it is desirable to identify the origination point of the undesired electrical impulses prior to ablation. Mapping may be accomplished by placing one or more mapping electrodes into contact with the tissue in question. Mapping of tissue may occur by placing one or more mapping electrodes into contact with the endocardial surface of the heart and/or the epicardial surface of the heart. Therefore, a need exists for a mapping instrument that is capable of mapping the heart, e.g., during an ablation procedure. Preferably, this mapping instrument, as initially presented to a surgeon, would be indifferent to rotational orientation, and further would be capable of independently maintaining a number of different shapes as desired by the surgeon.

As used herein, the term "mapping instrument" includes a hand-held instrument capable of pacing and/or mapping cardiac tissue. The mapping instrument is similar to the electrosurgical instrument described above in that it is relatively short (as compared to a catheter-based device), and rigidly couples an electrode tip to the instrument's handle that is otherwise held and manipulated by the surgeon. The rigid construction of the mapping instrument requires direct, open access to the targeted tissue. Thus, for mapping and/or pacing of cardiac tissue via the mapping instrument, it is desirable to gain access to the patient's heart through one or more openings in the patient's chest (such as a sternotomy, a thoracotomy, a small incision and/or a port). In addition, the patient's heart may be opened through one or more incisions, thereby allowing access to the endocardial surface of the heart.

Once the target site (e.g., right atrium, left atrium, right ventricle, left ventricle, epicardial surface, endocardial surface, pulmonary veins, etc.) is accessible, the surgeon positions the electrode tip of the mapping instrument at the target site. The surgeon can easily control positioning and movement of the tip, as the mapping instrument is rigidly constructed and relatively short (in contrast to a catheter-based technique).

In cardiac resynchronization therapy (CRT) for the treatment of patients with congestive heart failure and ventricular dysynchrony, the heart is paced from both ventricles simultaneously by placing two ventricular leads on opposite sides of the heart. Various studies have shown that lead location: can affect cardiac function; therefore, optimizing placement of the left ventricular lead on the left ventricular free wall may improve CRT results and patient outcomes.

Venous anatomy may not allow a transveous lead to be placed in an optimal location. However, an epicardial lead may be placed at any site on the heart, creating the opportunity to optimize lead position. There are several situations during implantation of a left ventricular lead in which one should consider converting from a transveous lead procedure to an epicardial lead procedure. These include inability to cannulate the coronary sinus or the desired coronary vein, inability of the lead to properly lodge in the vein or lack of any vein in the preferred location.

Interest in optimizing left ventricular lead placement for cardiac resynchronization therapy is being supported by growing data that demonstrate the location of the lead on the heart can affect hemodynamics and improve patient outcomes. Epicardial mapping is a technique to determine a patient-specific location for the left-sided pacing lead in CRT procedures.

SUMMARY OF THE INVENTION

One aspect of the present invention relates to a system for ablating cardiac tissue comprising an electrosurgical instrument and a mapping instrument. The electrosurgical instrument includes an elongated shaft and a non-conductive handle. The shaft defines a proximal section, a distal section, and an internal lumen extending from the proximal section. The distal section forms an electrically conductive rounded tip and defines at least one passage fluidly connected to the lumen. This passage distributes fluid from the internal lumen outwardly from the shaft. Further, the shaft is adapted to be transitionable from a straight state to a bent state, preferably a number of different bent states. In this regard, the shaft is capable of independently maintaining the distinct shapes associated with the straight state and the bent state(s). The non-conductive handle is rigidly coupled to the proximal section of the shaft. With this in mind, an exterior surface of the shaft distal the handle and proximal the distal section is electrically non-conductive. In one preferred: embodiment, the shaft is comprised of an elongated electrode body and an electrical insulator. The electrode body defines the distal section and is rigidly coupled to the handle. The electrical insulator surrounds at least a portion of the electrode body proximal the distal section such that the tip is exposed.

During use, and when first presented to a surgeon, the shaft is in the straight state such that the electrosurgical instrument is effectively indifferent to a rotational orientation when the handle is grasped by the surgeon. Subsequently, the surgeon can bend the shaft to a desired shape (i.e., the bent state) being most useful for the particular electrosurgical procedure. During the procedure, a conductive fluid is directed onto the target site from the internal lumen via the passage. The tip then energizes the dispensed fluid, causing tissue ablation or cauterization.

The mapping instrument also includes an elongated shaft and a non-conductive handle. The shaft defines a proximal section and a distal section. The distal section forms an electrically conductive rounded tip. Like the electrosurgical instrument, the shaft of the mapping instrument is adapted to be transitionable from a straight state to a bent state, preferably a number of different bent states. In this regard, the shaft is capable of independently maintaining the distinct shapes associated with the straight state and the bent state(s). The non-conductive handle is rigidly coupled to the proximal section of the shaft. With this in mind, an exterior surface of the shaft distal the handle and proximal the distal section is electrically non-conductive. In one preferred embodiment, the shaft is comprised of an elongated electrode body and an electrical insulator. The electrode body defines the distal section and is rigidly coupled to the handle. The electrical insulator surrounds at least a portion of the electrode body proximal the distal section such that the tip is exposed.

During use, and when first presented to a surgeon, the shaft is in the straight state such that the mapping instrument is effectively indifferent to a rotational orientation when the handle is grasped by the surgeon. Subsequently, the surgeon can bend the shaft to a desired shape (i.e., the bent state) being most useful for the particular medical procedure.

Yet another aspect of the present invention relates to an ablation system including an electrosurgical instrument, a source of conductive fluid, an energy source and a mapping instrument. The electrosurgical instrument includes an elongated shaft and a non-conductive handle. The shaft defines a proximal section, a distal section, and an internal lumen extending from the proximal section. The distal section forms an electrically conductive rounded tip and defines at least one passage fluidly connected to the lumen. Further, the shaft is adapted to be transitionable from, and independently maintain a shape in, a straight state and a bent state. The handle is rigidly coupled to the proximal section of the shaft. An exterior surface of the shaft distal the handle and proximal the distal section is electrically non-conductive. The source of conductive fluid is fluidly connected to the internal lumen. Finally, the energy source is electrically connected to the tip. During use, the electrosurgical instrument can be presented to the target site in either the straight state or the bent state. Regardless, the shaft independently maintains the shape associated with the selected state. Conductive fluid is delivered from the conductive fluid source to the internal lumen, and is then distributed to the target site via the passage. The energy source is activated, thereby energizing the electrode tip. This action, in turn, energizes the distributed conductive fluid, causing desired tissue ablation or cauterization. In one preferred embodiment, the electrosurgical system further includes an indifferent, or non-ablating, electrode (such as a grounding patch). The indifferent electrode is electrically connected to the energy source and it is placed separately from the target site. For example, the indifferent electrode may be placed on the back of the patient. The mapping instrument also includes an elongated shaft and a non-conductive handle. The shaft defines a proximal section and a distal section. The distal section forms an electrically conductive rounded tip. Further, the shaft is adapted to be transitionable from, and independently maintain a shape in, a straight state and a bent state. The handle is rigidly coupled to the proximal section of the shaft. An exterior surface of the shaft distal the handle and proximal the distal section is electrically non-conductive. Finally, the energy source is electrically connected to the tip. During use, the mapping instrument can be presented to the target site in either the straight state or the bent state. Regardless, the shaft independently maintains the shape associated with the selected state. The energy source is activated, thereby energizing the electrode tip. This action, in turn, causes desired tissue to be stimulated. In one preferred embodiment, the electrosurgical system further includes an indifferent, or non-ablating, electrode (such as a needle electrode). The indifferent electrode is electrically connected to the energy source and it is placed separately from the target site.

Yet another aspect of the present invention relates to a method of performing an electrosurgical procedure. The method includes providing an electrosurgical instrument and a mapping instrument both including an elongated shaft and, a handle. In this regard, the shaft of the electrosurgical instrument defines a proximal section, a distal section, and an internal lumen. The proximal section is rigidly coupled to the handle, whereas the distal section forms a round tip. Finally, the internal lumen extends from the proximal section and is in fluid communication with at least one passage formed in the distal section. An exterior surface of the shaft distal the handle and proximal the distal section is electrically non-conductive. The shaft is provided in an initial straight state that otherwise defines a linear axis. The shaft is then bent to a first bent state in which a portion of the shaft is deflected relative to the linear axis. In this regard, the shaft independently maintains a shape of the first bent state. The shaft of the mapping instrument defines a proximal section and a distal section. The proximal section is rigidly coupled to the handle, whereas the distal section forms a round tip. An exterior surface of the shaft distal the handle and proximal the distal section is electrically non-conductive. The shaft is provided in an initial straight state that otherwise defines a linear axis. The shaft is then bent to a first bent state in which a portion of the shaft is deflected relative to the linear axis. In this regard, the shaft independently maintains a shape of the first bent state. The tip of the electrosurgical instrument is positioned at a tissue target site. In one preferred embodiment, an indifferent electrode is placed in contact with the patient. Conductive fluid is dispensed from the passage to the tissue target site via the internal lumen. Finally, energy is applied to the dispensed fluid by energizing the tip. Subsequently, the energized tip and conductive fluid ablates or cauterizes tissue at the tissue target site. In one embodiment, the tissue target site comprises tissue of a patient's heart, and the method further includes accessing the tissue target site through one or more openings in the patient's chest. In another embodiment, after a first lesion pattern is formed at a first tissue target site, the shaft is bent to a second shape and the procedure repeated to effectuate a second lesion pattern at a second tissue target site. In one embodiment, the tip of the mapping is positioned at a tissue target site comprising tissue of a patient's heart, and the method further includes accessing the tissue target site through one or more openings in the patient's chest.

Yet another aspect of the present invention relates to a method of performing an electrosurgical procedure. The method comprises providing; an instrument having an elongated shaft and a handle, the shaft defining a proximal section rigidly coupled to the handle, a distal section forming an electrically conductive tip; positioning the tip through a patient's chest; applying ablation energy to the tip while contacting cardiac tissue; creating an ablation lesion to isolate an area of cardiac tissue; stopping the application of ablation energy to the tip; repositioning the tip; and applying stimulation energy to the tip while contacting the area of isolated cardiac tissue to assess transmurality of the ablation lesion. The method further comprises an internal lumen extending from the proximal section of the shaft and in fluid communication with at least one passage formed in the distal section of the shaft. Conductive fluid is dispensed from the internal lumen of the shaft via the at least one passage while applying ablation energy to the tip. In one embodiment, the ablation energy is radiofrequency energy.

Yet another aspect of the present invention relates to a method of performing a left sided epicardial lead placement procedure. The method, comprises providing an instrument including an elongated shaft and a handle, the shaft defining a proximal section rigidly coupled to the handle, a distal section forming an electrically conductive tip; positioning the tip through a patient's chest to contact a first area of epicardial tissue of the patient's left ventricle; applying stimulation energy to the patient's right ventricle; recording the time at which a depolarization wave is sensed over the left ventricle following stimulation of the right ventricle; repositioning the tip to contact a second area of epicardial tissue of the patient's left ventricle; reapplying stimulation energy to the patient's right ventricle; recording the time at which the depolarization wave is sensed over the left ventricle following restimulation of the right ventricle; placing an epicardial lead in contact with the area of tissue that had the longest time interval at which the depolarization wave was sensed over the left ventricle following stimulation of the right ventricle. Once the optimal lead location site has been determined, it can visually marked by using adjacent anatomical landmarks. The mapping instrument is removed and an epicardial pacing lead implanted at that site.

DESCRIPTION OF THE PREFERRED EMBODIMENTS

Figure 1:
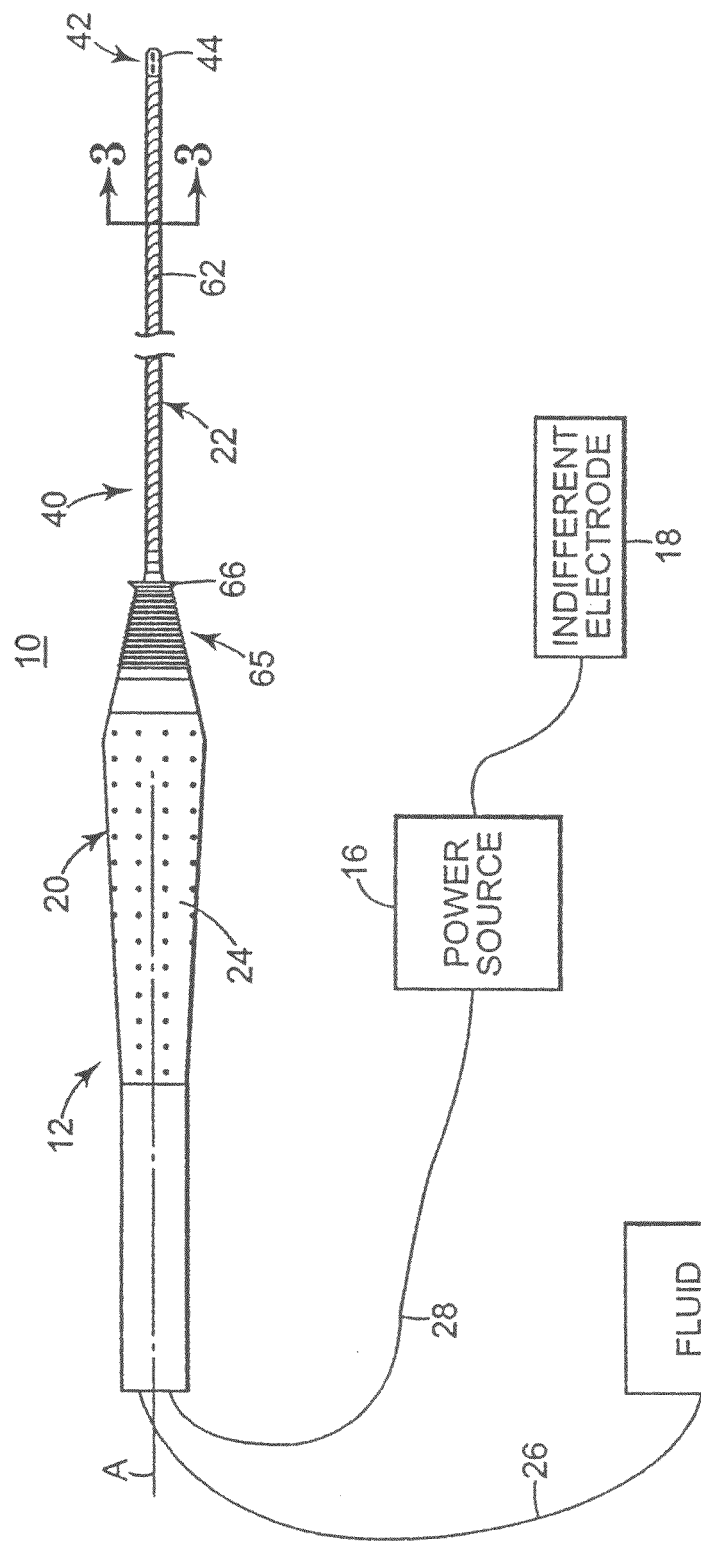
FIG. 1 is a side view of an electrosurgical system in accordance with the present invention, including portions shown in block form.

One preferred embodiment of an electrosurgical system 10 in accordance with the present invention is shown in FIG. 1.

The system 10 is comprised of an electrosurgical instrument 12, a fluid source 14, a power source 16, and an indifferent electrode 18. The various components are described in greater detail below. In general terms, however, the fluid source 14 is fluidly connected to the electrosurgical instrument 12. Similarly, the power source 16 is electrically connected to the electrosurgical instrument 12 and to the indifferent electrode 18. During use, conductive fluid is delivered from the fluid source 14 to a distal portion of the electrosurgical instrument 12. The distributed fluid is energized by the electrosurgical instrument 12 via the power source 16. The so-energized conductive fluid is capable of forming a virtual electrode, which is capable of ablating or cauterizing contacted tissue.

Figure 5A:
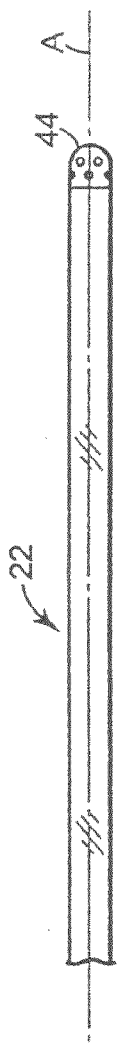
FIGS. 5A-5C are side views of the electrosurgical instrument of FIG. 1, illustrating exemplary shapes available during use of the electrosurgical instrument.
Figure 5B:
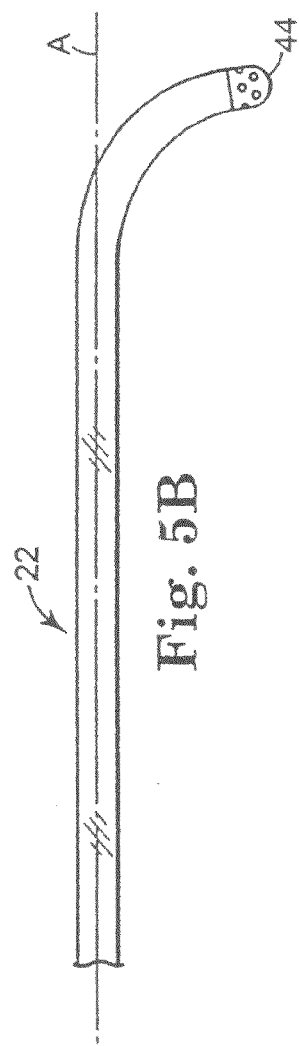
Figure 5C:

The electrosurgical instrument 12 includes a handle 20 and a shaft 22. As described in greater detail below, the shaft 22 is rigidly coupled to the handle 20, and is transitionable from a straight state (as illustrated in FIG. 1) to a bent state (for example as shown in FIGS. 5B and 5C). In this regard, the shaft 22 independently maintains the shape associated with the particular state (i.e., straight or bent).

The handle 20 is preferably made of a sterilizable, rigid, and non-conductive material, such as a polymer or ceramic. Suitable polymers include rigid plastics, rubbers, acrylics, nylons, polystyrenes, polyvinylchlorides, polycarbonates, polyurethanes, polyethylenes, polypropylenes, polyamides, polyethers, polyesters, polyolefins, polyacrylates, polyisoprenes, fluoropolymers, combinations thereof or the like. Further, the handle 20 is ergonomically designed to comfortably rest within a surgeon's hand (not shown). To this end, the handle 20 may include a grip portion 24 that is circular in cross section. This configuration facilitates grasping of the handle 20, and thus of the electrosurgical instrument 12, at any position along the grip portion 24 regardless of an overall rotational orientation of the electrosurgical instrument 12. That is to say, due to the circular, cross-sectional shape of the grip portion 24, the electrosurgical instrument 12 can be rotated to any position relative to a central axis A, and still be conveniently grasped by the surgeon. In an even more preferred embodiment, the grip portion 24 defines a gradual, distally increasing diameter that provides an orientation feature to help a surgeon identify where along the length of the electrosurgical instrument 12 he or she is grasping. For example, if the surgeon grasps the electrosurgical instrument 12 out of his visual sight during a medical procedure, the surgeon may identify based on the grip portion's 24 diameter where along the instrument he has grasped. Finally, the grip portion 24 is preferably formed of a low durometer polymer. Suitable polymers include low durometer plastics, rubbers, silicones, acrylics, nylons, polystyrenes, polyvinylchlorides, polycarbonates, polyurethanes, polyethylenes, polypropylenes, polyamides, polyethers, polyesters, polyolefins, polyacrylates, polyisoprenes, fluoropolymers, combinations thereof or the like. The grip portion 24 alternatively may be a sponge-like or foam-like material, such as an open-cell material or a closed-cell material.

Figure 2:
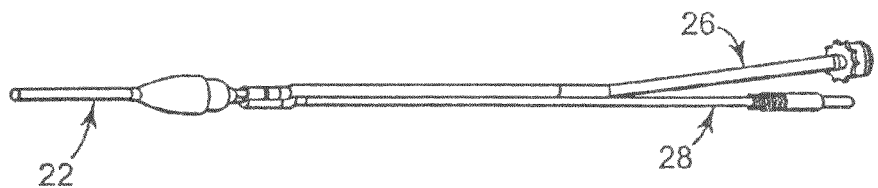
FIG. 2 is a perspective view of an electrosurgical instrument portion of the system of FIG. 1, with a handle removed.

Regardless of exact configuration, the handle 20 forms or encompasses one or more central lumens (not shown). The lumen(s) provides a pathway for a line or tubing 26 from the fluid source 14 to the shaft 22, as well as a pathway for a line or wiring 28 from the power source 16 to the shaft 22. In this regard, FIG. 2 illustrates the electrosurgical instrument 12 with the handle 20 removed. The tubing 26 from the fluid source 14 (FIG. 1) is shown as extending to, and being fluidly connected with, the shaft 22. Similarly, the line 28 from the power source 16 (FIG. 1) is shown as extending to, and being electrically connected with, the shaft 22.

Returning to FIG. 1, the shaft 22 is an elongated, relatively rigid component defining a proximal section 40 and a distal section 42. The distal section 42 terminates in an electrically conductive tip 44. As described in greater detail below, the tip 44 is rounded, defining a uniform radius of curvature. With this configuration, the tip 44 is, similar to the handle 20, indifferent to rotational orientation of the electrosurgical device 12. That is to say, regardless of how a surgeon (not shown) grasps the handle 20 (i.e., the rotational position of the handle 20 relative to the central axis A), a profile of the tip 44 in all directions (e.g., in front of the surgeon's thumb position, behind the surgeon's thumb position, etc.) is always the same so that the tip 44 is readily maneuvered along tissue (not shown) in any direction. To this end, the rounded shape facilitates sliding movement of the tip 44 along the tissue.

Figure 3:
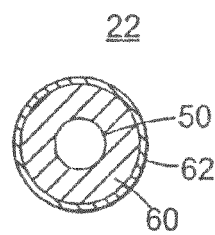
FIG. 3 is an enlarged, cross-sectional view of a portion of an electrosurgical instrument of FIG. 1 taken along the line 3-3.

With additional reference to FIG. 3, the shaft 22 defines an internal lumen 50 that is fluidly connected to the tubing 26. In this way, the internal lumen 50 delivers fluid from the fluid source 14 to the distal section 42.

Figure 4A:
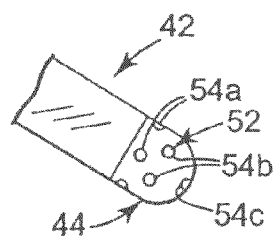
FIG. 4A is an enlarged, perspective view of a distal portion of the electrosurgical instrument of FIG. 1.

With additional reference to FIG. 4A, the distal section 42 preferably forms a plurality of passages 52 that are fluidly connected to the internal lumen 50. The passages 52 are formed at or proximal the tip 44 and preferably are uniformly located relative to a circumference of the distal section 42. For example, in one preferred embodiment, two sets 54a, 54b of the passages 52 are provided, in addition to a central passage 54c at the tip 44. The passages 52 associated with each of the two sets 54a, 54b are circumferentially aligned, and uniformly spaced approximately 90° from one another. For example, in one embodiment, the passages 52 are uniformly located on a hemispherical portion of the tip 44 as described below. Alternatively, other numbers and locations are acceptable. By preferably uniformly spacing the passages 52, however, the distal section 42 is further formed to be indifferent to rotational orientation of the electrosurgical instrument 12. In other words, regardless of the rotational position of the electrosurgical instrument 12 and/or the direction of tip 44 movement, the passages 52 provide a relatively uniform disbursement of conductive fluid about the tip 44 via the internal lumen 50. In an alternative embodiment, the tip 44 is made of a porous material, that allows fluid to pass from the internal lumen 50 through the tip 44.

Figure 4B:
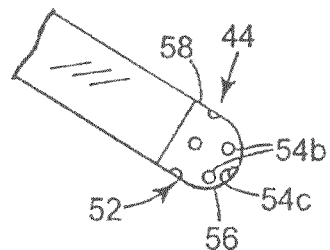
FIG. 4B is an enlarged, perspective view of a distal portion of an alternative embodiment electrosurgical instrument in accordance with the present invention.

In another alternative embodiment, and as best shown in FIG. 4B, at least some of the passages 52 (for example, the passage set 54b) are located along a generally hemispherical portion 56 of the tip 44. This one preferred design facilitates a more complete delivery of liquid to a target site (not shown) that is otherwise contacted by the tip 44. In general terms, during an electrosurgical procedure, it is important that a sufficient volume of irrigation fluid is continually provided to the electrode tip 44/target site tissue interface to reduce the opportunity for tissue charring or desiccation. Previous electrosurgical designs positioned all of the passages 52 (except for the central passage 54c) along a cylindrical portion 58 of the tip 44 (as opposed to the generally hemispherical portion 56). With this prior design, where a particular surgical procedure required that the tip 44 be oriented such that the passages 52 are "below" the electrode tip 44/target site tissue interface, some or all of the irrigation liquid otherwise dispensed from the passages 52 (other than the central passage 54c) might flow away from the electrode tip 44 (or back along the shaft 22). The one preferred passage configuration of FIG. 4B overcomes this concern, as all of the irrigation liquid distributed from the passages 54b on the generally hemispherical portion 56 will be delivered to the electrode tip 44/target site tissue interface due to surface tension at the interface.

Regardless of passage location, a further preferred feature of the shaft 22 is a malleable or shapeable characteristic. In particular, and with additional reference to FIGS. 5A-5C, the shaft 22 is configured to be transitionable from an initial straight state (FIG. 5A) to a bent or curved state (FIGS. 5B and 5C). In this regard, the electrosurgical instrument 12, and in particular the shaft 22, is initially presented to a surgeon (not shown) in the straight state of FIG. 5A, whereby the shaft 22 assumes a straight shape defining the central axis A. In the straight state, the shaft 22 is indifferent to rotational orientation, such that the electrosurgical instrument 12 can be grasped at any rotational position and the tip 44 will be located at an identical position. Further, as previously described, a profile of the tip 44 is also uniform or identical at any rotational position of the electrosurgical instrument 12. Subsequently, depending upon the constraints of a particular electrosurgical procedure, the shaft 22 can be bent relative to the central axis A. Two examples of an applicable bent state or shape are provided in FIGS. 5B and 5C. In a preferred embodiment, the shaft 22 can be bent at any point along a length thereof, and can be formed to include multiple bends or curves. Regardless, the shaft 22 is configured to independently maintain the shape associated with the selected bent shape. That is to say, the shaft 22 does not require additional components (e.g., pull wires, etc.) to maintain the selected bent shape. Further, the shaft 22 is constructed such that a user can readily re-shape the shaft 22 back to the straight state of FIG. 5A and/or other desired bent configurations. Notably, the shaft 22 is configured to relatively rigidly maintain the selected shape such that when a sliding force is imparted onto the shaft 22 as the tip 44 dragged across tissue, the shaft 22 will not overtly deflect from the selected shape.

In one preferred embodiment, the above-described characteristics of the shaft 22 are achieved by forming the shaft 22 to include an elongated electrode body 60 and an electrical insulator covering 62 as shown in FIGS. 1 and 3. The electrode body 60 defines the proximal section 40 and the distal section 42 of the shaft 22. To this end, the proximal section 40 of the electrode body 60 is rigidly coupled to the handle 20. The insulator 62 covers a substantial portion of the electrode body 60, preferably leaving the distal section 42 exposed. In particular, the insulator 62 is positioned to encompass an entirety of the electrode body 60 distal the handle 20 and proximal the distal section 42 (and in particular, proximal the passages 52 and the tip 44).

In one preferred embodiment, the electrode body 60 is a tube formed of an electrically conductive, malleable material, preferably stainless steel, however other materials such as, for example, nitinol can be used. The passages 52 are preferably drilled, machined, laser cut, or otherwise formed through at least a portion of the electrode body 60. The passages or openings 52 may comprise circular holes, semi-circular holes, oval holes, rectangular slots, and/or other configurations for allowing fluid to pass.

The insulator 62 is formed of one or more electrically non-conductive materials, and serves to electrically insulate the encompassed portion of the electrode body 60. Multiple layers of electrically non-conductive materials can help prevent the likelihood of forming an electrical short along the length of the electrode body 60 due to a mechanical failure of one of the non-conductive materials. In this regard, the insulator 62 is preferably comprised of two materials having considerably different mechanical properties, e.g., a silicone and a fluoropolymer. In one preferred embodiment, a silicone tubing material is overlaid with a heat shrink fluoropolymer tubing material. Alternatively, the insulator 62 may be one or more non-conductive coatings applied over a portion of the electrode body 60. In addition to being non-conductive, the insulator 62 is preferably flexible and conforms to the electrode body 60 such that the insulator 62 does not impede desired shaping and re-shaping of the electrode body 60 as previously described.

It will be understood that the preferred construction of the shaft 22 to include the elongated electrode body 60 and the insulator 62 is but one available configuration. Alternatively, the shaft 22 can be constructed of an electrode material forming the tip 44, and a rigid or malleable, non-conductive tube rigidly connecting the tip 44 to the handle 20. The non-conductive tube can include one or more metal conductors, such as straight wire and/or windings for electrically connecting the tip 44 to the power source 16. Along these same lines, another alternative embodiment includes forming the tip 44 from an inherently porous material. For example, the tip 44 may comprise one or more porous polymers, metals, or ceramics. Further, the tip 44 may be coated with non-stick coatings such as PTFE or other types of coatings such as biological coatings. Another alternative embodiment includes construction of the shaft 22 to include one or more metal conductors, such as straight wire and/or windings inside a rigid or malleable non-conductive polymer tube. The non-conductive polymer tube includes one or more openings, such as holes, slots or pores (preferably corresponding with the passages 52 previously described), which allow conductive fluid to exit the polymer tube. The conductive fluid creates a virtual electrode via electrically connecting the one or more metal conductors to the target tissue. Conversely, the shaft 22 may comprise a polymer tube having one or more openings, such as holes, slots or pores (preferably corresponding with the passages 52 previously described), placed inside an electrical conductor, such as a metal tube having one or more openings, such as holes, slots or pores, or a metal winding having a spacing that allows conductive fluid to pass through, to control conductive fluid delivery through the electrical conductor. Finally, the insulator 62 may cover a portion of the metal tube or windings.

Figure 6:
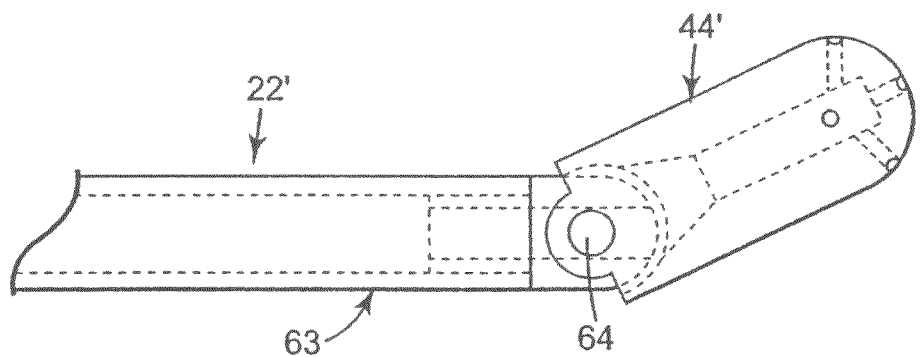
FIG. 6 is an enlarged, side view of a portion of an alternative embodiment electrosurgical instrument in accordance with the present invention.

With respect to the above-described alternative embodiments, connection between the elongated tube and the separate tip 44 can be accomplished in a variety of manners. Once again, the elongated tube can comprise a conductive or non-conductive material(s), such as metal(s) or plastic(s). The elongated tube can be connected to the tip 44 via a variety of coupling techniques, including, for example, welding, laser welding, spin welding, crimping, gluing, soldering and press fitting. Alternatively, the distal end of the elongated tube and the tip 44 can be configured to threadably engage one another and/or mechanical engagement members) (e.g., pins, screws, rivets, etc.) can be employed. In another embodiment, the elongated tube is rigidly coupled to the tip 44. In yet another embodiment, the tip 44 can be moveably coupled to the elongated tube, whereby the tip 44 can be moved and/or locked relative to the elongated tube. For example, the tip 44 can be coupled to the elongated tube via one or more; joints or hinges. The joints or hinges can be ball joints and/or joints that include a pin. To this end, a pin-type joint can be configured to allow the tip 44 to swivel relative to the elongated, tube. Further, the joint(s) can be configured to move and lock into position. In addition, one or more actuators (e.g., knobs, buttons, levers, slides, etc.) can be located on, for example, the handle 20 (FIG. 1) for actuating the joint(s). With the above in mind, FIG. 6 illustrates a portion of an alternative embodiment shaft 22' including a tip 44' moveably coupled to an elongated tube 63 by a pin 64.

Returning to FIG. 1, the electrosurgical instrument 12 preferably includes a coupling member 65 for rigidly coupling the shaft 22 to the handle 20. The coupling member 65 can comprise one or more polymers, plastics, and/or rubbers. For example, the coupling member 65 can comprise one or more silicones, acrylics, nylons, polystyrenes, polyvinylchlorides, polycarbonates, polyurethanes, polyethylenes, polypropylenes, polyamides, polyethers, polyesters, polyolefins, polyacrylates, polyisoprenes, fluoropolymers, combinations thereof or the like. The coupling member 65 preferably forms a drip edge 66 to interrupt, divert and prevent any flow of liquid from the tip 44, down the shaft 22 and onto the handle 20, thereby preventing any electrically conducting fluid from contacting the surgeon.

Regardless of exact construction of the electrosurgical instrument 12, the fluid source 14 maintains a supply of conductive fluid (not shown), such as an energy-conducting fluid, an ionic fluid, a saline solution, a saturated saline solution, a Ringer's solution, etc. It is preferred that the conductive fluid be sterile. The conductive fluid can further comprise one or more contrast agents, and/or biological agents such as diagnostic agents, therapeutic agents or drugs. The biological agents may be found in nature (naturally occurring) or may be chemically synthesized.

As a point of reference, during use the conductive fluid serves to electrically couples the electrode tip 44 of electrosurgical instrument 12 to the tissue to be treated, thereby lowering the impedance at the target site. The conductive fluid may create a larger effective electrode surface. The conductive fluid can help cool the tip 44 of the electrosurgical instrument 12. The conductive fluid may keep the surface temperature of the tip 44 below the threshold for blood coagulation, which may clog the electrosurgical instrument 12. The conductive fluid may also cool the surface of the tissue thereby preventing over heating of the tissue which can cause popping, desiccation, burning and/or charring of the tissue. The burning and/or charring of the tissue may also clog the electrosurgical instrument 12. Therefore, use of the conductive fluid may reduce the need to remove a clogged electrosurgical instrument for cleaning or replacement. Further, charred tissue has high impedance, thereby making the transfer of RF energy difficult, and may limit the ability of the electrosurgical instrument 12 to form a transmural lesion. The delivery of conductive fluid during the electrosurgical process may help create deeper lesions that are more likely to be transmural. Transmurality is achieved when the full thickness of the target tissue is ablated. Continuous conductive fluid flow may ensure that a conductive fluid layer between the tip 44 and the contours of the tissue to be treated is created.

In one preferred embodiment, the fluid source 14 includes a fluid reservoir, such as a bag, a bottle or a canister, for maintaining a supply of conductive fluid previously described. With this configuration, the fluid reservoir can be positioned at an elevated location, thereby gravity feeding the conductive fluid to the electrosurgical instrument 12, or the fluid reservoir may be pressurized, thereby pressure feeding the conductive fluid to the electrosurgical instrument 12. For example, a pressure cuff may be placed around a flexible bag, such as an IV bag, of conductive fluid, thereby pressure feeding the conductive fluid to the electrosurgical instrument 12. Alternatively, the fluid source 14 can include, and/or be connected to, a manual or electrical pump (not shown), such as an infusion pump, a syringe pump, or a roller pump. The fluid source 14 can further comprise one or more orifices or fluid regulators, (e.g., valves, fluid reservoirs, conduits, lines, tubes and/or hoses) to control flow rates. The conduits, lines, tubes, or hoses may be flexible or rigid. For example, a flexible hose may be used to communicate fluid from the fluid source 14 to the electrosurgical instrument 12, thereby allowing electrosurgical instrument 12 to be easily manipulated by a surgeon. Alternatively, the fluid source 14 can be directly connected to, or incorporated into, the handle 20. For example, a pressurized canister of conductive fluid may be directly connected to the handle 20. Further, the fluid source 14 can comprise a syringe, a squeeze bulb and/or some other fluid moving means, device or system.

In another embodiment, the fluid source 14 further includes a surgeon-controlled switch (not shown). For example, a switch may be incorporated in or on the fluid source 14 or any other location easily and quickly accessed by a surgeon for regulation of conductive fluid delivery. The switch may be, for example, a hand switch, a foot switch, or a voice-activated switch comprising voice-recognition technologies.

In yet another alternative embodiment, the fluid source 14 includes a visual and/or audible signaling device (not shown) used to alert a surgeon to any change in the delivery of conductive fluid. For example, a beeping tone or flashing light can be used to alert the surgeon that a change has occurred in the delivery of conductive fluid.

The power source 16 is of a type known in the art, and is preferably a radio-frequency (RF) generator. The generator can be powered by AC current, DC current or it can be battery powered either by a disposable or re-chargeable battery. The generator can incorporate a controller (not shown) or any suitable processor to control power levels delivered to the electrosurgical instrument 12 based on information supplied to the generator/controller.

The above-described electrosurgical system 10, including the electrosurgical instrument 12, is useful for a number of different tissue ablation and cauterization procedures. For example, the electrosurgical system 10 can be used to remove hemorrhoids or varicose veins or stop esophageal bleeding to name but a few possible uses. Additionally, the electrosurgical system 10 is highly useful for the surgical treatment of cardiac arrhythmia, and in particular treatment of atrial fibrillation via ablation of atrial tissue. To this end, the Maze procedure, such as described in *Cardiovascular Device Update*, Vol. 1, No. 4, July 1995, pp. 2-3, the teachings of which are incorporated herein by reference, is a well known technique, whereby lesion patterns are created along specified areas of the atria. The Maze III procedure, a modified version of the original Maze procedure, has been described in *Cardiac Surgery Operative Technique*, Mosby Inc., 1997, pp. 410-419, the teachings of which are incorporated herein by reference. In an effort to reduce the complexity of the surgical Maze procedure, a modified Maze procedure was developed as described in *The Surgical Treatment of Atrial Fibrillation*, Medtronic Inc., 2001, the teachings, of which are incorporated herein by reference.

Figure 7A:
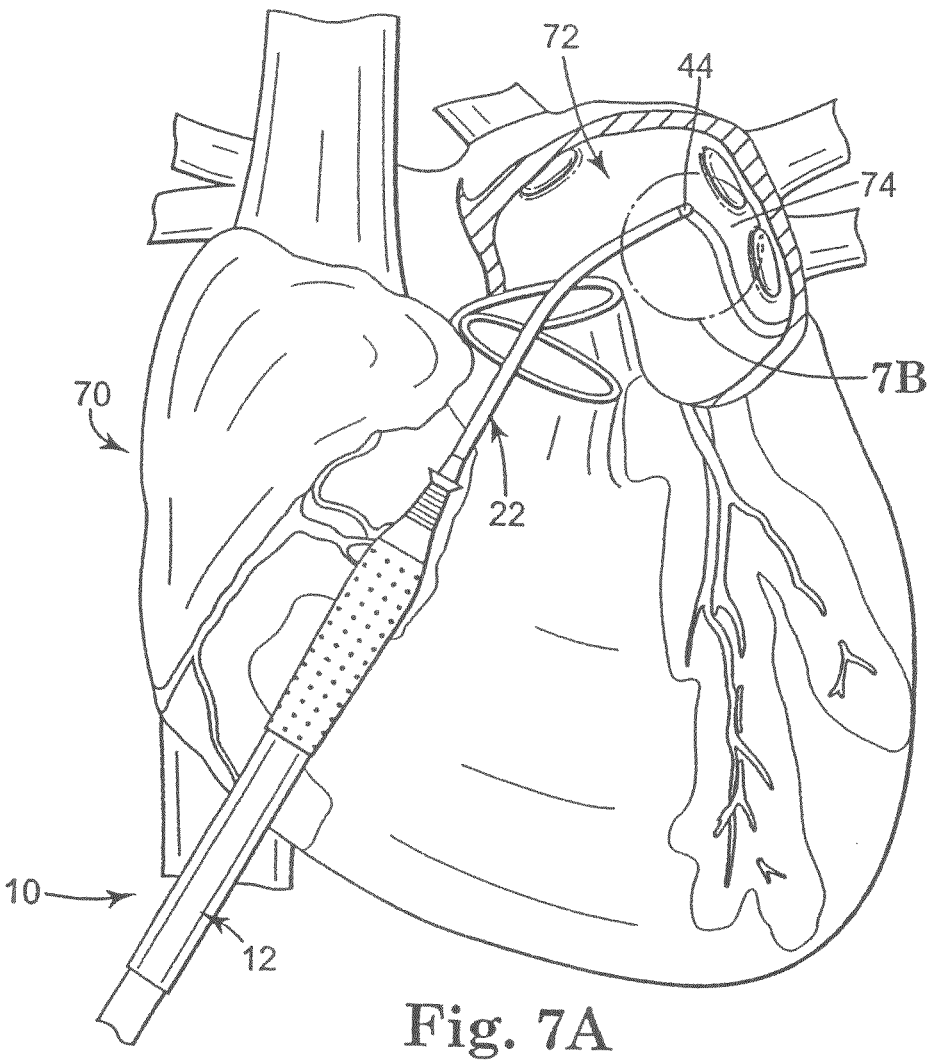
FIG. 7A is a cut-away illustration of a patient's heart depicting use of an electrosurgical instrument in accordance with the present invention during a surgical ablation procedure.

FIG. 7A depicts use of the electrosurgical system 10, and in particular the electrosurgical instrument 12, performing a portion of the Maze procedure. In particular, FIG. 7A includes a representation of a heart 70 with its left atrium 72 exposed. Prior to use, the electrosurgical instrument 12 is provided to the surgeon (not shown) with the shaft 22 in the initial straight state (FIG. 1). The surgeon then evaluates the constraints presented by the tissue target site 74 and the desired lesion pattern to be formed. Following this evaluation, the surgeon determines an optimal shape of the shaft 22 most conducive to achieving the desired ablation/lesion pattern. With this evaluation in mind, the surgeon then transitions or bends the shaft 22 from the initial straight state to the bent state illustrated in FIG. 7A. Once again, the shaft 22 is configured to independently maintain this selected shape. The shaft 22 can be bent by hand and/or by use of bending jigs or tools.

Figure 7B:
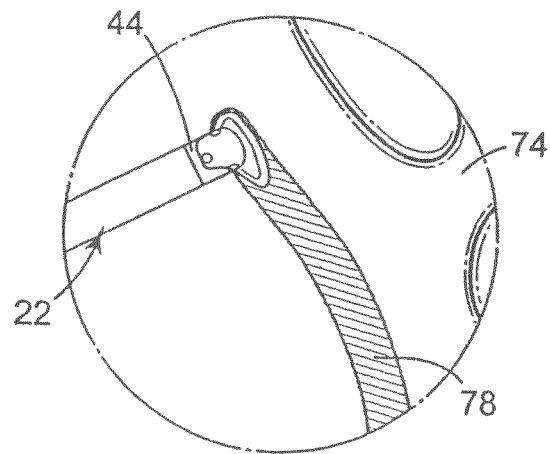
FIG. 7B is an enlarged illustration of a portion of FIG. 7A.

Once the desired shape of the shaft 22 has been achieved, the tip 44 is directed to the tissue target site 74. An indifferent electrode (18 in FIG. 1, but not shown in FIG. 7A) is placed in contact with the patient. Conductive fluid from the fluid source 14 (FIG. 1) is delivered to the tissue target site 74 via the internal lumen 50 (FIG. 3), the passages 52 and/or the porous tip 44. Once sufficient fluid flow has been established, the tip 44 is energized via the power source 16 (FIG. 1). The tip 44, in turn, energizes the distributed fluid, thereby creating a virtual electrode that ablates contacted tissue. The surgeon then slides or drags the tip 44 along the left atrium 70 tissue, thereby creating a desired lesion pattern 78, as best shown in FIG. 7B. In this regard, the rigid coupling between the shaft 22 and the handle 20 allows the tip 44 to easily be slid along the atrial tissue via movement of the handle 20. Once the desired lesion pattern 78 has been completed, energization of the tip 44 is discontinued, as well as delivery of conductive fluid from the fluid source 14. If additional lesion patterns are required, the surgeon again evaluates the target tissue site, and re-forms the shaft 22 accordingly.

Notably, the shaft 22 need not necessarily be bent to perform a tissue ablation procedure. Instead, the tip 44 can be drug across the target site tissue 74 with the shaft 22 in the initial straight state. In this regard, because the shaft 22 is straight and the handle 20 (FIG. 1) is preferably circumferentially uniform, the electrosurgical instrument 12 does not have a discernable drag direction (as compared to the shaft 22 being bent or curved, whereby the curve inherently defines a most appropriate drag direction).

In addition to the exemplary procedure described above, the electrosurgical instrument 12 may be positioned and used, for example, through a thoracotomy, through a sternotomy, percutaneously, transveneously, arthroscopically, endoscopically, for example, through a percutaneous port, through a stab wound or puncture, through a small incision, for example, in the chest, in the groin, in the abdomen, in the neck or in the knee, or in combinations thereof. It is also contemplated that the electrosurgical instrument 12 may be used in other ways, for example, in open-chest surgery on a heart in which the sternum is split and the rib cage opened with a retractor.

The electrosurgical system 10, and in particular the electrosurgical instrument 12, described above with respect to FIG. 1 is but one acceptable configuration in accordance with the present invention. That is to say, the system 10 and/or the instrument 12 can assume other forms and/or include additional features while still providing an electrosurgical instrument having a shaft that independently maintains varying shapes associated with a straight state and a bent state, and is indifferent to rotational orientation in the straight state.

For example, the electrosurgical instrument 12 can include a surgeon-controlled switch. For example, a switch may be incorporated in or on the electrosurgical instrument 12 or any other location easily and quickly accessed by the surgeon for regulation of the electrosurgical instrument 12 by the surgeon. The switch may be, for example, a hand switch, a foot switch, or a voice-activated switch comprising voice-recognition technologies. One or more switches may be incorporated into the grip portion 24 of the electrosurgical instrument 12. For example, a switch may be used to control conductive fluid delivery and/or power delivery. A switch incorporated into the grip portion 24 may be a switch, such as a membrane switch, encompassing the entire circumference of the electrosurgical instrument 12, thereby effectively being indifferent to a rotational orientation when the surgeon grasps the handle. That is to say, due to the cross-sectional shape of the switch, the electrosurgical instrument 12 may be rotated to any position relative to a central axis A, and still be conveniently controlled by the surgeon.

Alternatively, a hand switch connected to the electrosurgical instrument 12, but not incorporated into the electrosurgical instrument 12, may be used. For example, a switch designed to be worn by a surgeon, for example on a surgeon's thumb, may be used to activate and/or deactivate the electrosurgical instrument 12. A switch may be incorporated into a cuff or strap that is placed on or around the thumb or finger of a surgeon. Alternatively, a switch may be designed to fit comfortably in a surgeon's palm.

One or more visual and/or audible signals used to alert a surgeon to the completion or resumption of ablation, conductive fluid delivery and/or power delivery, for example, may be incorporated into the electrosurgical instrument 12. For example, a beeping tone or flashing light that increases in frequency as the ablation period ends or begins may be used. Alternatively or in addition, an indicator light otherwise located on the electrosurgical instrument can be inductively coupled to the power source 16 and adapted such that when power is being delivered to the electrosurgical instrument 12, the light is visible to the surgeon or other users.

Figure 8A:
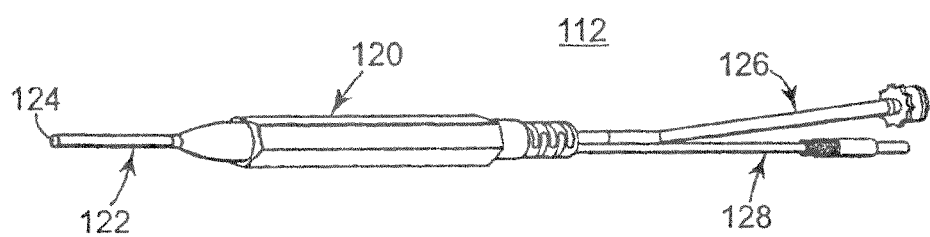
FIGS. 8A and 8B are side perspective views of an alternative electrosurgical instrument in accordance with the present invention.
Figure 8B:
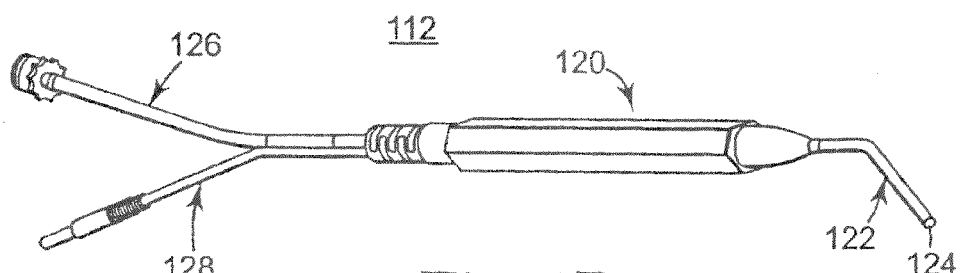

An alternative embodiment electrosurgical instrument 112 is provided in FIGS. 8A and 8D. The electrosurgical instrument 112 is highly similar to the electrosurgical instrument 12 (FIG. 1) previously described, and includes a handle 120, a shaft 122, a fluid supply tube 126 and wiring 128. The shaft 122 is virtually identical to the shaft 22 (FIG. 1) previously described, and forms a tip 124 having passages (not shown) fluidly connected to an internal lumen (not shown). Further, the shaft 122 is adapted to be bendable from a straight state (FIG. 8A) to multiple bent states (one of which is illustrated in FIG. 8B), with the shaft 122 independently maintaining a shape associated with the particular state. Similar to previous embodiments, the fluid supply tube 126 fluidly connects the fluid source 14 (FIG. 1) to the shaft 122, whereas the wiring 128 electrically connects the power source 16 (FIG. 1) to the shaft 122.

The handle 120 varies from the handle 20 (FIG. 1) previously described in that the handle 120 does not define a curved outer surface. Instead, the handle 120 is hexagonal in transverse cross-section. This alternative configuration is, however, indifferent to rotational orientation when grasped by a user, thereby promoting the preferred ease of use feature previously described. Notably, the handle 120 can alternatively be formed to a variety of other symmetrical transverse cross-sectional shapes (e.g., circular, octagonal, etc.).

In yet another alternative embodiment, the electrosurgical system 10 (FIG. 1) further includes a controller (not shown) that can also gather and process information from the electrosurgical instrument 12, 120, fluid source 14 and/or one or more sensors or sensing elements such as temperature sensors or probes. The information supplied to or gathered by the controller can be used to adjust, for example, conductive fluid delivery, power levels, and/or energization times. For example, a temperature sensor coupled to the controller can be located in the distal section 42 (FIG. 1) of the electrosurgical instrument 12. The temperature sensor can be a thermocouple element that measures the temperature of the tip 44 rather than the temperature of the conductive fluid or the temperature of the tissue being ablated. Alternatively, the temperature sensor can be a thermocouple element that measures the temperature of the conductive fluid or a thermocouple element that measures the temperature of the tissue being ablated. When the ablation site is being irrigated with a conductive fluid, the temperature of the tissue may differ to some degree from the temperature of the conductive fluid or the temperature of the tip 44.

Heat, 1.0 kcal/g, is required to raise the temperature of water, present at the ablation site, by 1° C. However, due to the unique chemical structure of the water molecule, additional heat is required for water to change phase from the liquid phase to the gaseous phase. If the temperature at the ablation site exceeds 100° C., water will change phase, boil and may result in an audible "steam pop" within the tissue. This pop may damage and even rupture the tissue. Therefore, it is desirable to prevent the ablation site from getting to hot. In addition, to form a permanent ablation lesion the temperature of the tissue at the ablation site must be elevated to approximately 50° C. or greater. For these reasons, it is desirable to use one or more temperature-sensing elements such as, for example, thermocouples, thermisters, temperature-sensing liquid crystals, temperature-sensing chemicals, thermal cameras, and/or infrared (IR) fiber optics, to monitor the temperature of the ablation site during the ablation procedure.

Figure 9A:
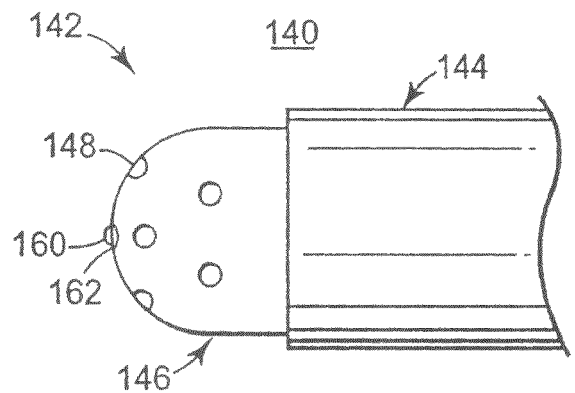
FIG. 9A is an enlarged, perspective view of a distal portion of an alternative embodiment electrosurgical instrument in accordance with the present invention.
Figure 9B:
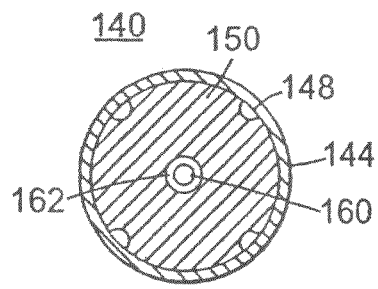
FIG. 9B is an enlarged, transverse, cross-sectional view of the electrosurgical instrument of FIG. 9A.
Figure 9C:
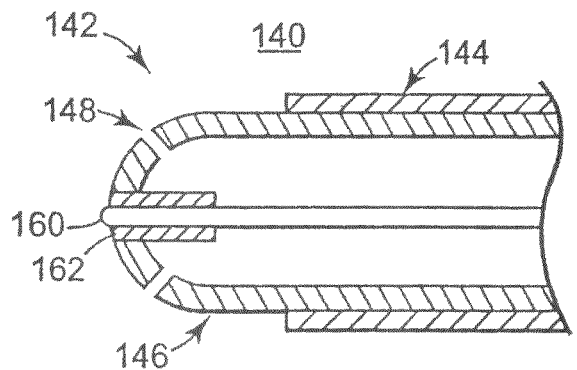
FIG. 9C is an enlarged, longitudinal, cross-sectional view of the electrosurgical instrument of FIG. 9A.

With the above in mind, FIGS. 9A-9C depict a portion of an alternative embodiment electrosurgical device 140, and in particular a distal section 142 thereof. The electrosurgical instrument 140 is highly similar to previous embodiments, and includes a shaft 144 terminating at an electrically conductive tip 146 having passages 148 formed therein that are fluidly connected to an internal lumen 150. Further, the electrosurgical instrument 140 includes a temperature probe 160 for monitoring tissue temperature of the tissue being ablated. The temperature probe 160 is placed at the tip 146. A ring of insulation material 162 may be used to electrically and thermally isolate the temperature probe 160 from the electrically conductive tip 146. The preferred central placement of the temperature probe 160 at the tip 146 allows the temperature probe 160 to directly contact a tissue surface in a number of orientations. The preferred insulating material 162 helps to prevent the thermal mass of the tip 146 and the RF energy from interfering with temperature information otherwise provided by the probe 160.

Figure 10B:
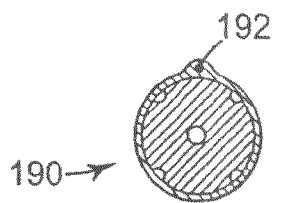
FIG. 10B is an enlarged, cross-sectional view of the electrosurgical instrument of FIG. 10A.
Figure 10A:
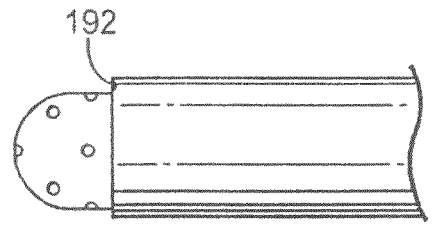
FIG. 10A is an enlarged, perspective view of a distal portion of an alternative embodiment electrosurgical instrument in accordance with the present invention.
Figure 10D:
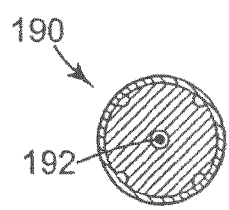
FIG. 10D is an enlarged, cross-sectional view of a portion of the electrosurgical instrument of FIG. 10C.
Figure 10C:
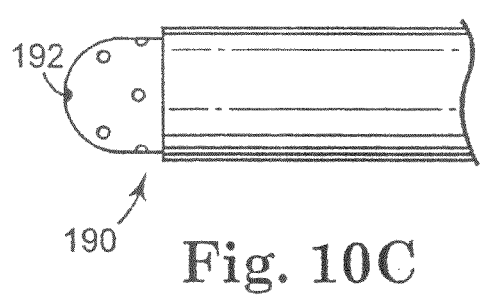
FIG. 10C is an enlarged, perspective view of a distal portion of an alternative embodiment electrosurgical instrument in accordance with the present invention.

An alternative embodiment for monitoring temperature includes an IR optical fiber system. As shown in FIGS. 10A-10D, an alternative embodiment electrosurgical instrument 190 may include an optical fiber 192 for monitoring temperature based on IR. The optical fiber 192 can be positioned adjacent a tip 194 otherwise defined by the instrument 190 (FIGS. 10A and 10B) or within the tip 194 itself (FIGS. 10C and 10D).

The above-described temperature-sensing elements 160, 192 can be used to adjust, for example, conductive fluid delivery, power levels, and/or ablation times. Temperature-sensing elements can be coupled to a visual and/or audible signal used to alert a surgeon to a variety of thermal conditions. For example, a beeping tone or flashing light that increases in frequency as temperature of the tissue, the conductive fluid and/or electrosurgical instrument is increased and/or as temperature exceeds a predetermined amount can be used.

Along these same lines, the above-mentioned controller can incorporate one or more switches to facilitate regulation of the various components of the electrosurgical system 10 (FIG. 1) by the surgeon. One example of such a switch is a foot pedal. The switch can also be, for example, a hand switch as described above, or a voice-activated switch comprising voice-recognition technologies. The switch can be incorporated in or on one of the surgeon's instruments, such as surgical site retractor, e.g., a sternal or rib retractor, or the electrosurgical instrument 12 (FIG. 1), or any other location easily and quickly accessed by the surgeon. The controller can also include a display or other means of indicating the status of various components to the surgeon, such as a numerical display, gauges, a monitor display or audio feedback.

Finally, a visual and/or audible signal used to alert a surgeon to the completion or resumption of ablation, sensing, monitoring, and/or delivery of conductive fluid can be incorporated into the controller. For example, a beeping tone or flashing light that increases in frequency as the ablation or electrocautery period ends or begins can be provided.

In yet another alternative embodiment, the fluid source 14 can be slaved to the electrosurgical instrument 12, the power source 16 and/or one or more sensors (as previously described). For example, the fluid source 14 can be designed to automatically stop or start the delivery of conductive fluid during the delivery of RF energy. Conversely, the delivery of RF energy may be slaved to the delivery of conductive fluid. That is the delivery of RF energy to the tip 44 would be coupled to the delivery of conductive fluid to the tip 44. If the flow of conductive fluid to the tip 44 were stopped, the RF energy delivered to the tip 44 would also automatically stop. For example, a switch responsive to the delivery of conductive fluid to the tip 44 for controlling RF energy delivery to the tip 44 can be incorporated into the electrosurgical instrument 12. The switch can be located, for example, within the shaft 22 or the handle 20 of electrosurgical instrument 12.

Figure 11:
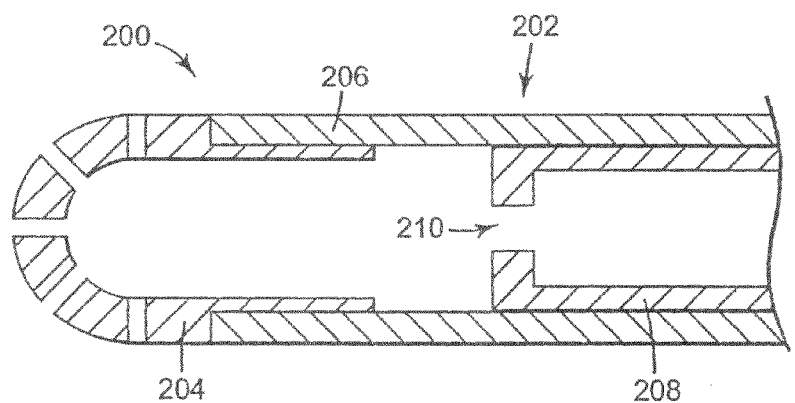
FIG. 11 is an enlarged, cross-sectional view of a portion of an alternative embodiment electrosurgical instrument in accordance with the present invention.

With the above in mind, FIG. 11 illustrates a portion of an alternative embodiment electrosurgical instrument 200 including a shaft 202 extending from a handle (not shown). The shaft 202 includes an electrically conductive tip 204 and a malleable, non-conductive tube 206 rigidly connecting the tip 204 to the handle. An electrically conducting switch piston 208 is located within the non-conductive tube 206. The conducting switch piston 208 is electrically coupled to the power source 16 (FIG. 1). The conducting switch piston 208 is movably held in a non-contacting position relative to the tip 204 by a spring or other elastic means (not shown). As conductive fluid is delivered, a pressure develops behind an orifice 210 of the conducting switch piston 208. The size and shape of the orifice 210 is selected based on expected fluid delivery rates and pressures. When the necessary pressure or force to over come the spring retaining pressure or force is reached, the conducting switch 208 travels distally towards the tip 204, thereby making an electrical contact with the tip 204. Other means can be used to slave the delivery of power to the tip 204 of the electrosurgical instrument 200 to the delivery of conductive fluid to the tip 204 of the electrosurgical instrument 200. For example, the controller can incorporate one or more switches to facilitate the regulation of RF energy based on the delivery of conductive fluid.

Figure 12:
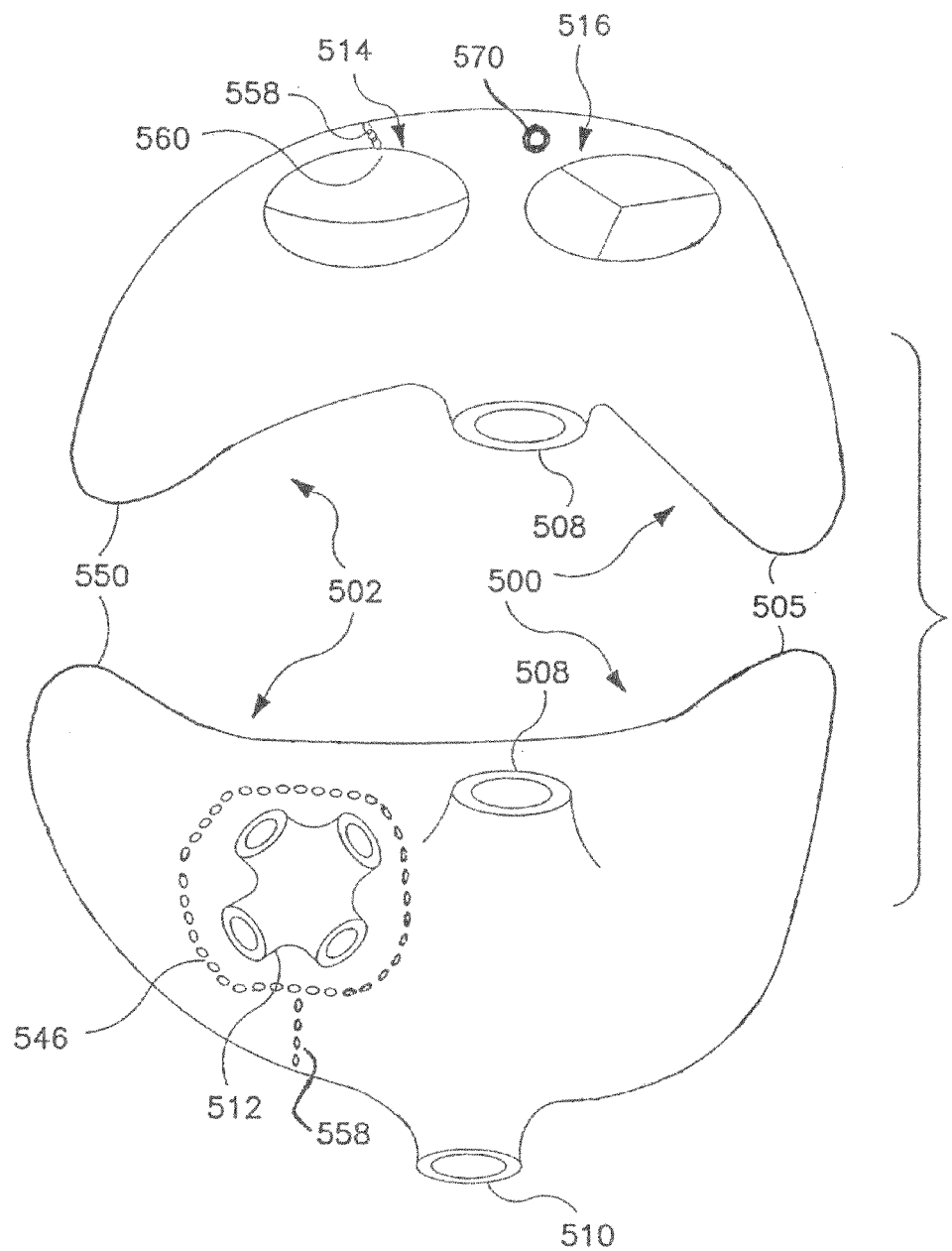
FIG. 12 is a schematic view illustrating an ablation lesion produced in accordance with the present invention.
Figure 13:
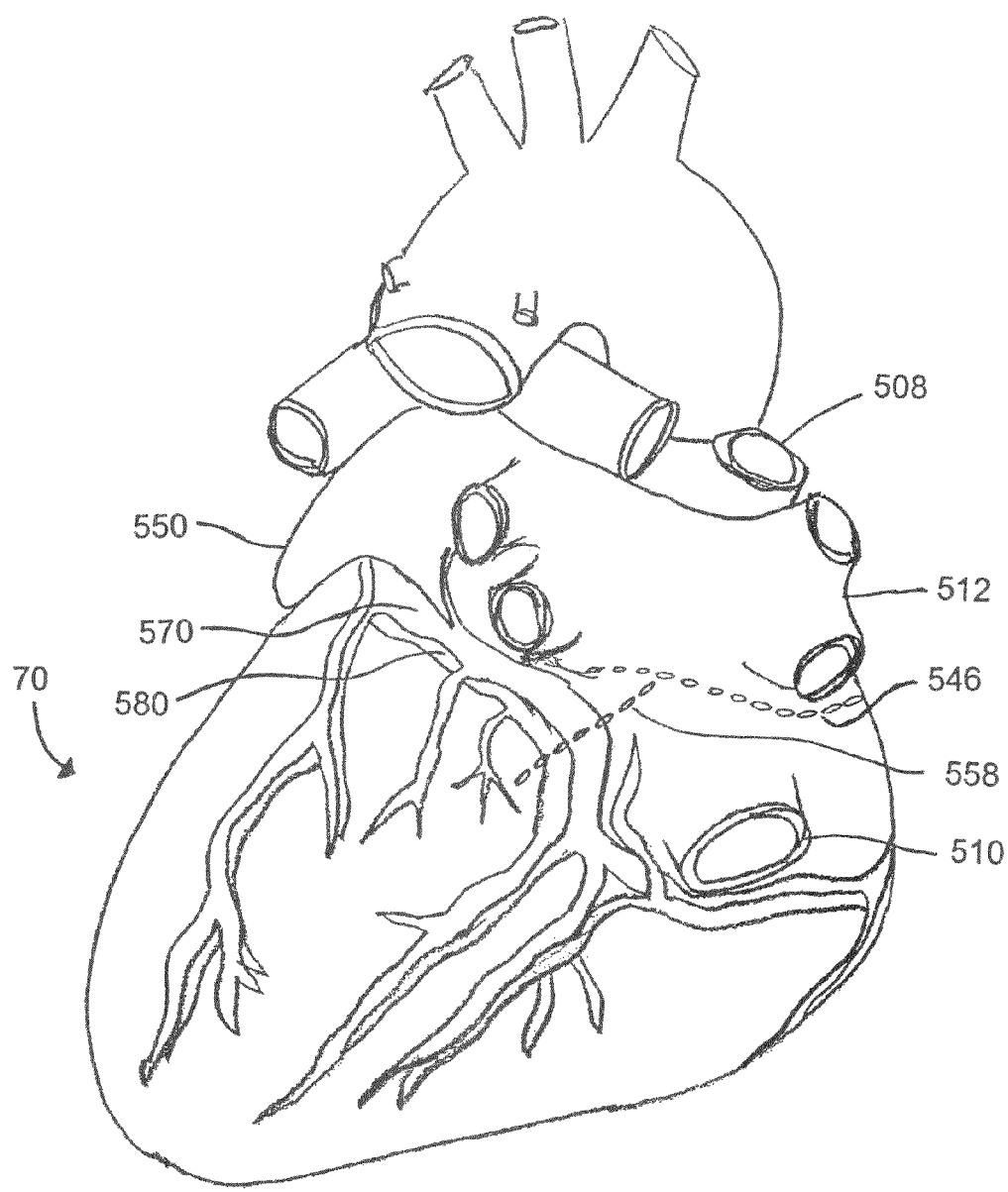
FIG. 13 is a schematic view illustrating an ablation lesion produced in accordance with the present invention.

The incision patterns of a Maze III procedure are described in the book '*Cardiac Surgery Operative Technique*' Donald B. Doty, M.D. at pages 410-419, incorporated herein by reference in its entirety, and hereafter referred to as the "Doty Reference." The left atrial isthmus lesion 558 (see FIG. 12) extends from a pulmonary vein isolation lesion 546, inferior of the pulmonary veins, crosses over the coronary sinus and ends at the mitral valve annulus 560. The lesion 558 corresponds to the incision illustrated as step S as described in the Doty reference. The lesion 558 may be created via an epicardial or endocardial approach. The lesion may also be created via a coronary sinus approach comprising the advancement of electrode tip 44 of electrosurgical instrument 12 into the coronary sinus 570. In particular, FIG. 12 is a schematic drawing illustrating the right and left atria, 500, 502, respectively, as viewed from a lower aspect, including tricuspid valve 516, orifice of coronary sinus 570, and mitral valve 514 and as viewed from a more superior aspect, including the bases of the pulmonary veins 512 and the bases of the superior vena cava and inferior vena cava, 508, 510, respectively, which enter the right atrium 500. The right and left atrial appendages are also illustrated schematically at 505 and 550, respectively. FIG. 13 is a schematic drawing illustrating the lesion 558 crossing over the coronary sinus 570 and the circumflex artery 580 as viewed from a posterior view of the heart 70.

Prior to the ablation procedure, the surgeon evaluates the constraints presented for advancing electrode tip 44 into the coronary sinus 570 from within the right atrium 500. Following this evaluation, the surgeon determines an optimal shape of the shaft 22 most conducive to achieving the desired ablation lesion from within the coronary sinus 570. With this evaluation in mind, the surgeon then transitions or bends the shaft 22 into a desired state. Once again, the shaft 22 is configured to independently maintain the selected shape.

Once the desired shape of the shaft 22 has been achieved, the tip 44 is advanced into the right atrium 500 and into the coronary sinus 570. Ablating tip 44 may be advanced into the right atrium 500 through an incision, i.e., an atriotomy (not shown). If the heart is beating, i.e., the heart is not on cardiopulmonary bypass, a purse-string suture may be used to minimize blood loss through the incision and around the device. Once inside the right atrium 500, tip 44 is advanced into the coronary sinus 570 until tip 44 reaches the desired location within the coronary sinus for creation of the ablation lesion 558. Proper ablative tip placement can be confirmed by palpitation of the coronary sinus, for example, in an open-chest procedure. For procedures wherein the coronary sinus cannot be palpitated, electrosurgical instrument 12 may include one or more additional features. For example, electrosurgical instrument 12 may include a pressure monitoring sensor or port, thereby allowing one to monitor pressure during placement and use of the device. Pressures of the right atrium and the coronary sinus may be used to confirm proper placement of the ablative tip 44 in the coronary sinus. Alternatively, an echo enhancing feature or material may be added to electrosurgical instrument 12 thereby allowing the proper placement of the tip 44 into the coronary sinus to be confirmed via transesophageal echocardiography (TEE). Alternatively, electrosurgical instrument 12 may include one or more light sources for lighting tip 44. An endoscope could then be used to visually confirm proper placement of tip 44 in the coronary sinus since the light emanating from the tip would shine through the thin tissue wall of the coronary sinus. Once tip 44 is advanced into the coronary sinus at the proper depth or distance, conductive fluid from the fluid source 14 (FIG. 1) is delivered to the ablation area via the internal lumen 50 (FIG. 3), the passages 52 and/or the porous tip 44. Once sufficient fluid flow has been established, tip 44 is energized via the power source 16 (FIG. 1). The tip 44, in rum, energizes the distributed fluid, thereby creating a virtual electrode that ablates contacted tissue within the coronary sinus. Once the lesion 558 has been completed, energization of the tip 44 is discontinued, as well as delivery of conductive fluid from the fluid source 14. If additional lesions are required, the surgeon again evaluates the target tissue site, and re-forms the shaft 22 accordingly.

It is contemplated that the ablation lesion 558 may be created via placement of one or more ablative elements within the coronary sinus. In addition, it is contemplated that one or more ablative energies may be used with one or more ablative elements to create ablation lesion 558, for example, radiofrequency energy, ultrasound energy, laser energy, microwave energy, and/or combinations thereof, may be used. Alternatively, one or more cryo ablation elements could be placed within the coronary sinus to form lesion 558.

In yet another embodiment, and with general reference to FIG. 1, the electrosurgical instrument 12, the fluid source 14 and/or the power source 16 can be slaved to a robotic system or a robotic system may be slaved to the electrosurgical instrument 12, the fluid source 14 and/or the power source 16.

The electrosurgical system, and in particular the electrosurgical instrument, of the present invention provides a marked improvement over previous designs. The handle and shaft are configured to be indifferent to rotational orientation when initially presented to a surgeon. Subsequently, the surgeon can conveniently shape or bend the shaft so as to provide a shape most conducive to forming the lesion pattern required by the particular surgical procedure. In this regard, the shaft independently maintains the selected shape throughout the particular electrosurgical procedure. Subsequently, the shaft can be re-shaped back to a straight configuration, or to any other desired curvature.

Figure 14:
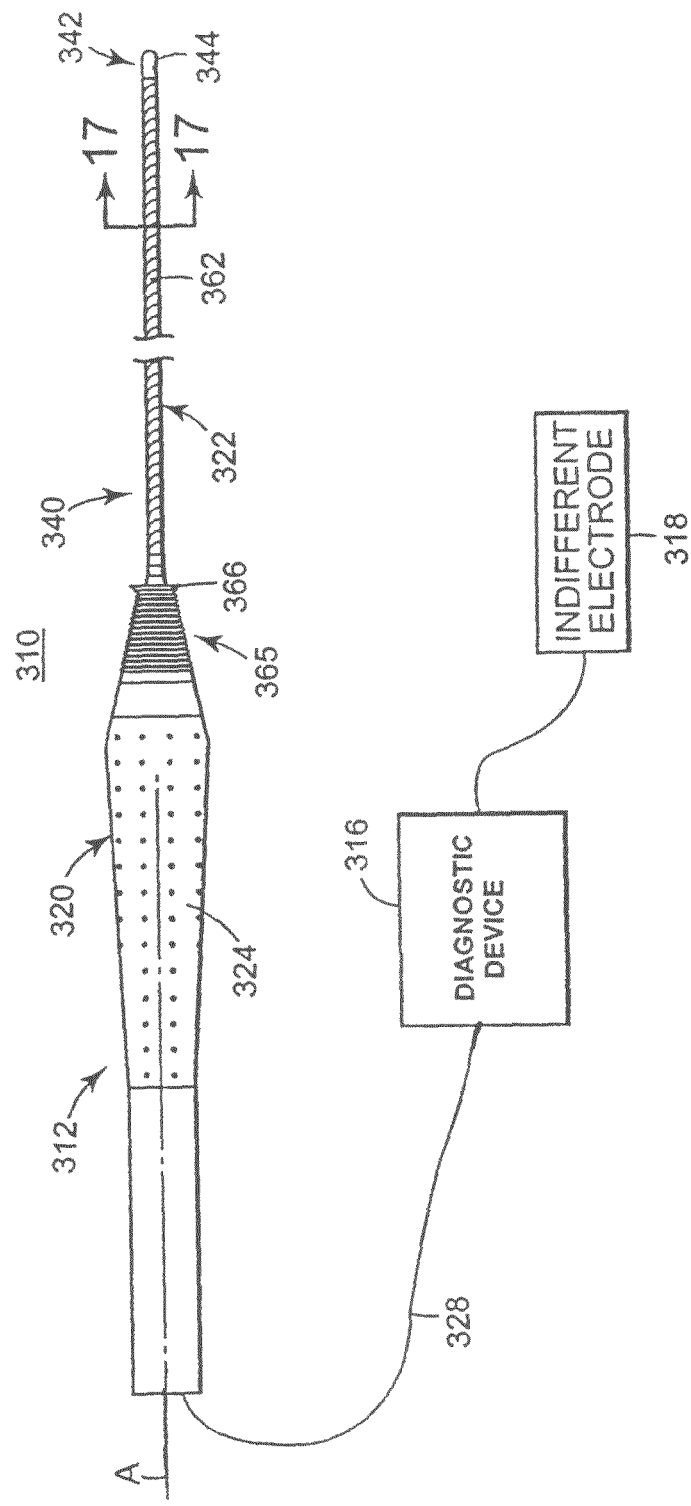
FIG. 14 is a side view of a mapping system in accordance with the present invention, including portions shown in block form.

One embodiment of a mapping system 310 in accordance with the present invention is shown in FIG. 14. The system 310 is comprised of a mapping instrument 312, a diagnostic device 316 and an indifferent electrode 318. The various components are described in greater detail below. In general terms, the diagnostic device 316 is electrically connected to the mapping instrument 312 and to the indifferent or grounding electrode 318. In one embodiment, die diagnostic device 316 may be the Medtronic Programmer/Analyzer model 2090/2290 which has the capability of pacing and sensing.

Figure 15A:
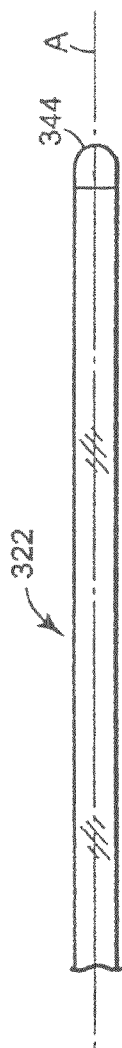
FIGS. 15A-15C are side views of the mapping instrument of FIG. 14, illustrating exemplary shapes available during use of the mapping instrument.
Figure 15B:
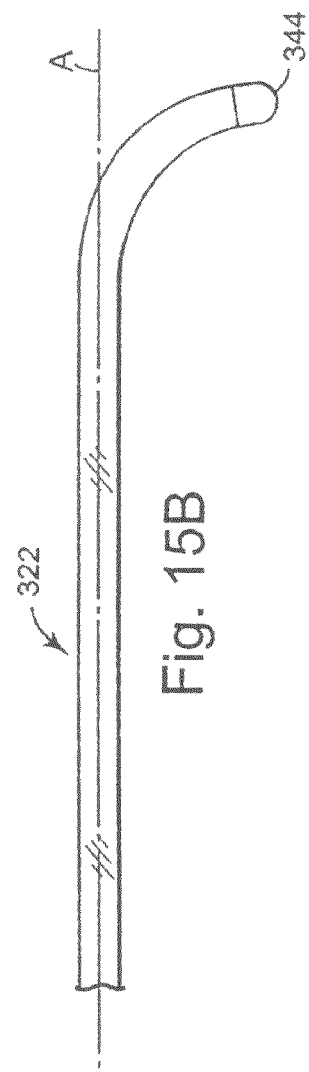
Figure 15C:
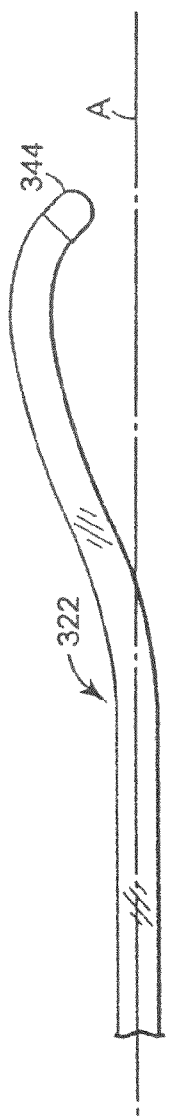

The mapping instrument 312 includes a handle 320 and a shaft 322. As described in greater detail below, the shaft 322 is rigidly coupled to the handle 320, and is transitionable from a straight state (as illustrated in FIGS. 14 and 15A) to a bent state (for example as shown in FIGS. 15B and 15C). In this regard, the shaft 322 independently maintains the shape associated with the particular state (i.e., straight or bent).

The handle 320 is preferably made of a sterilizable, rigid, and non-conductive material, such as a polymer or ceramic. Suitable polymers include rigid plastics, rubbers, acrylics, nylons, polystyrenes, polyvinylchlorides, polycarbonates, polyurethanes, polyethylenes, polypropylenes, polyamides, polyethers, polyesters, polyolefins, polyacrylates, polyisoprenes, fluoropolymers, combinations thereof or the like. Further, the handle 20 is economically designed to comfortably rest within a surgeon's hand (not shown). To this end, the handle 320 may include a grip portion 324 that is circular in cross section. This configuration facilitates grasping of the handle 320, and thus of the mapping instrument 312, at any position along the grip portion 324 regardless of an overall rotational orientation of the mapping instrument 312. That is to say, due to the circular, cross-sectional shape of the grip portion 324, the mapping instrument 312 can be rotated to any position relative to a central axis A, and still be conveniently grasped by the surgeon. In one embodiment, the grip portion 324 defines a gradual, distally increasing diameter that provides an orientation feature to help a surgeon identify where along the length of the mapping instrument 312 he or she is grasping. For example, if the surgeon grasps the mapping instrument 312 out of his visual sight during a medical procedure, the surgeon may identify based on the grip portion's 324 diameter where along the instrument he has grasped. Finally, the grip portion 324 may be formed of a low durometer polymer. Suitable polymers include low durometer plastics, rubbers, silicones, acrylics, nylons, polystyrenes, polyvinylchlorides, polycarbonates, polyurethanes, polyethylenes, polypropylenes, polyamides, polyethers, polyesters, polyolefins, polyacrylates, polyisoprenes, fluoropolymers, combinations thereof or the like. The grip portion 324 alternatively may be a sponge-like or foam-like material, such as an open-cell material or a closed-cell material.

Figure 16:
FIG. 16 is a perspective view of a mapping instrument portion of the system of FIG. 14, with a handle removed.

Regardless of exact configuration, the handle 320 may form or encompass one or more central lumens (not shown). The lumen(s) can provide a pathway for a line or wiring 328 from the diagnostic device 316 to the shaft 322. In this regard, FIG. 16 illustrates the mapping instrument 312 with the handle 320 removed. The line 328 from the diagnostic device 316 (FIG. 14) is shown as extending to, and being electrically connected with, the shaft 322.

Returning to FIG. 14, the shaft 322 is an elongated, relatively rigid component defining a proximal section 340 and a distal section 342. The distal section 342 terminates in an electrically conductive tip 344. As described in greater detail below, the tip 344 may be rounded, defining a uniform radius of curvature. In one embodiment, the tip 344 may be shaped like a round ball. The tip 344 may be textured. With the tip being in a rounded configuration, the tip 344 is, similar to the handle 320, indifferent to rotational orientation of the mapping device 312. That is to say, regardless of how a surgeon (not shown) grasps the handle 320 (i.e., the rotational position of the handle 320 relative to the central axis A), a profile of the tip 344 in all directions (e.g., in front of the surgeon's thumb position, behind the surgeon's thumb position, etc.) is always the same so that the tip 344 is readily maneuvered along tissue (not shown) in any direction. To this end, the rounded shape can facilitate a sliding movement of the tip 344 along the tissue.

A preferred feature of the shaft 322 is a malleable or shapeable characteristic. In particular, and with additional reference to FIGS. 15A-15C, the shaft 322 is configured to be transitionable from an initial straight state (FIG. 15A) to a bent or curved state (FIGS. 15B and 15C). In this regard, the mapping instrument 312, and in particular the shaft 322, is initially presented to a surgeon (not shown) in the straight state of FIG. 15A, whereby the shaft 322 assumes a straight shape defining the central axis A. In the straight state, the shaft 322 is indifferent to rotational orientation, such that the mapping instrument 312 can be grasped at any rotational position and the tip 344 will be located at an identical position. Further, as previously described, a profile of the tip 344 is also uniform or identical at any rotational position of the mapping instrument 312. Subsequently, depending upon the constraints of a particular mapping procedure, the shaft 322 can be bent relative to the central axis A. Two examples of an applicable bent state or shape are provided in FIGS. 15B and 15C. In a preferred embodiment, the shaft 322 can be bent at any point along a length thereof, and can be formed to include multiple bends or curves. Regardless, the shaft 322 is configured to independently maintain the shape associated with the selected bent shape. That is to say, the shaft 322 does not require additional components (e.g., pull wires, etc.) to maintain the selected bent shape. Further, the shaft 322 is constructed such that a user can readily re-shape the shaft 322 back to the straight state of FIG. 15A and/or other desired bent configurations. Notably, the shaft 322 is configured to relatively rigidly maintain the selected shape such that when a force is imparted onto the shaft 322 as the tip 344 contacts tissue, the shaft 322 will not overtly deflect from the selected shape.

Figure 17:
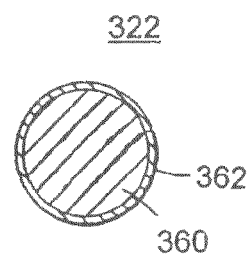
FIG. 17 is an enlarged, cross-sectional view of a portion of a mapping instrument of FIG. 14 taken along the line 17-17.

In one preferred embodiment, the above-described characteristics of the shaft 322 are achieved by forming the shaft 322 to include an elongated electrode body 360 and an electrical insulator covering 362 as shown in FIGS. 14 and 17. The electrode body 360 defines the proximal section 340 and the distal section 342 of the shaft 322. To tins end, the proximal section 340 of the electrode body 360 is rigidly coupled to the handle 320. The insulator 362 covers a substantial portion of the electrode body 360, preferably leaving the distal section 342 exposed. In particular, the insulator 362 is positioned to encompass an entirety of the electrode body 360 distal the handle 320 and proximal the distal section 342 (and in particular, proximal the tip 344).

In one preferred embodiment, the electrode body 360 is formed of an electrically conductive, malleable material, preferably stainless steel, however other materials such as, for example, nitinol can be used. The insulator 362 is formed of one or more electrically non-conductive materials, e.g., a nonconductive fluoropolymer, and serves to electrically insulate the encompassed portion of the electrode body 360. Multiple layers of electrically non-conductive materials can help prevent the likelihood of forming an electrical short along the length of the electrode body 360 due to a mechanical failure of one of the non-conductive materials. In this regard, the insulator 362 is preferably comprised of two materials having considerably different mechanical properties, e.g., a silicone and a fluoropolymer. In one embodiment, a silicone tubing material is overlaid with a heat shrink fluoropolymer tubing material. Alternatively, the insulator 362 may be one or more non-conductive coatings applied over a portion of the electrode body 360. In addition to being non-conductive, the insulator 362 is preferably flexible and conforms to the electrode body 360 such that the insulator 362 does not impede desired shaping and re-shaping of the electrode body 360 as previously described.

It will be understood that the preferred construction of the shaft 322 to include the elongated electrode body 360 and the insulator 362 is but one available configuration. Alternatively, the shaft 322 can be constructed of an electrode material forming the tip 344, and a rigid or malleable, non-conductive rod or tube rigidly connecting the tip 344 to the handle 320. The non-conductive rod or tube can include one or more metal conductors, such as straight, wire and/or windings for electrically connecting the tip 344 to the diagnostic device 316. The tip 344 may be coated with one or more coatings. Another alternative embodiment includes construction of the shaft 322 to include one or more metal conductors, such as straight wire and/or windings inside a rigid or malleable non-conductive polymer tube. The insulator 362 may cover a portion of the wire or windings.

Figure 18:
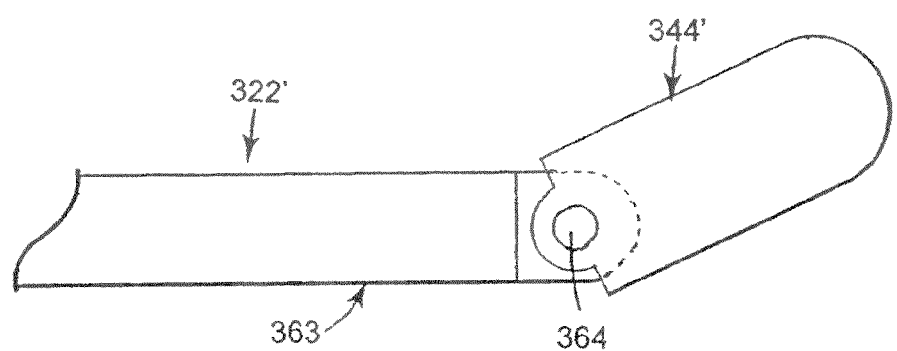
FIG. 18 is an enlarged, side view of a portion of an alternative embodiment of a mapping instrument in accordance with the present invention.

With respect to the above-described alternative embodiments, connection between the elongated rod or tube and the separate tip 344 can be accomplished in a variety of manners. Once again, the elongated rod or tube can comprise a conductive or non-conductive material(s), such as metal(s) or plastic(s). The elongated rod or tube can be connected to the tip 344 via a variety of coupling techniques, including, for example, welding, laser welding, spin welding, crimping, gluing, soldering and press fitting. Alternatively, the distal end of the elongated rod or tube and the tip 344 can be configured to threadably engage one another and/or mechanical engagement member(s) (e.g., pins, screws, rivets, etc.) can be employed. In another embodiment, the elongated rod or tube is rigidly coupled to the tip 344. In yet another embodiment, the tip 344 can be moveably coupled to the elongated rod or tube, whereby the tip 344 can be moved and/or locked relative to the elongated rod or tube. For example, the tip 344 can be coupled to the elongated rod or tube via one or more joints or hinges. The joints or hinges can be ball joints and/or joints that include a pin. To this end, a pin-type joint can be configured to allow the tip 344 to swivel relative to the elongated rod or tube. Further, the joint(s) can be configured to move and lock into position. In addition, one or more actuators (e.g., knobs, buttons, levers, slides, etc.) can be located on, for example, the handle 320 (FIG. 1) for actuating the joint(s). With the above in mind, FIG. 18 illustrates a portion of an alternative embodiment shaft 322' including a tip 344' moveably coupled to an elongated rod or tube 363 by a pin 364.

Returning to FIG. 14, the mapping instrument 312 preferably includes a coupling member 365 for rigidly coupling the shaft 322 to the handle 320. The coupling member 365 can comprise one or more polymers, plastics, and/or rubbers. For example, the coupling member 365 can comprise one or more silicones, acrylics, nylons, polystyrenes, polyvinylchlorides, polycarbonates, polyurethanes, polyethylenes, polypropylenes, polyamides, polyethers, polyesters, polyolefins, polyacrylates, polyisoprenes, fluoropolymers, combinations thereof or the like.

Figure 19A:
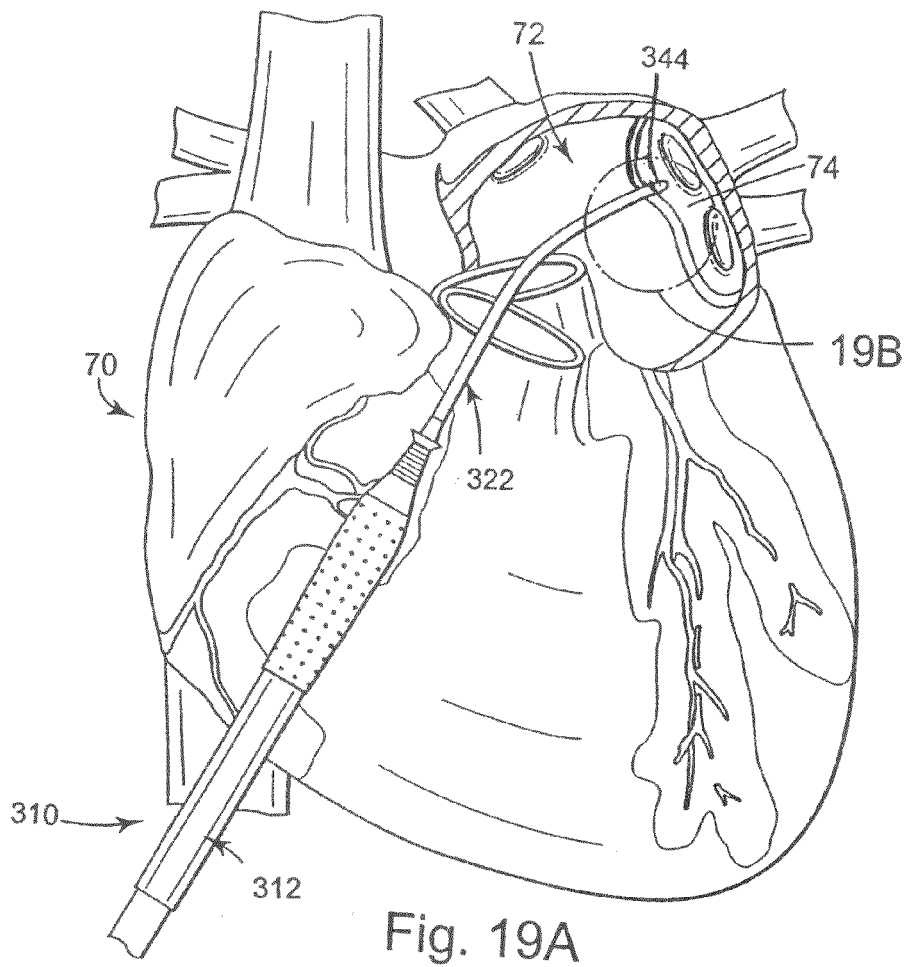
FIG. 19A is a cut-away illustration of a patient's heart depicting use of a mapping instrument in accordance with the present invention during a surgical ablation procedure.

FIG. 19A depicts use of the mapping system 310, and in particular, the mapping instrument 312, performing an assessment of transmurality of one or more ablation lesions 78 created by an ablation tool, for example electrosurgical instrument 12. Transmurality is achieved when the full thickness of the target tissue is ablated. In particular, FIG. 19A includes a representation of a heart 70 with its left atrium 72 exposed. Prior to use, the mapping instrument 312 is provided to the surgeon (not shown) with the shaft 322 in the initial straight state (FIG. 14). The surgeon then evaluates the constraints presented by the tissue target site 74 and the lesion pattern 78 formed earlier by an ablation procedure. Following this evaluation, the surgeon determines an optimal shape of the shaft 322 most conducive to achieving the desired assessment. With this evaluation in mind, the surgeon then transitions or bends the shaft 322 from the initial straight state to the bent state illustrated in FIG. 19A. Once again, the shaft 322 is configured to independently maintain this selected shape. The shaft 322 can be bent by hand and/or by use of bending jigs or tools.

Once the desired shape of the shaft 322 has been achieved, the tip 344 is directed to the tissue target site 74. A grounding electrode (318 in FIG. 14, but not shown in FIG. 19A) is placed in contact with the patient. The grounding electrode may comprise a needle electrode and a cable for connection to the diagnostic device 316. Alternatively, a grounding wire may be coupled to diagnostic device 316 and a metal retractor coupled to the patient. For example, a metal sternal retractor used to spread a patient's ribs may be used as a grounding electrode.

If additional lesions are to be assessed, the surgeon again evaluates the target tissue site, and re-forms the shaft 322 accordingly. Notably, the shaft 322 heed not necessarily be bent to perform a tissue mapping/pacing procedure. Instead, the tip 344 can contact the target site tissue 74 with the shaft 322 in the initial straight state. In this regard, because the shaft 322 is straight and the handle 320 (FIG. 14) is preferably circumferentially uniform, the mapping instrument 312 does not have a discernable use direction (as compared to the shaft 322 being bent or curved, whereby the curve inherently defines a most appropriate use direction).

In addition to the one exemplary procedure described above, the mapping instrument 312 may be positioned and used, for example, through a thoracotomy, through a sternotomy, percutaneously, transveneously, endoscopically, for example, through a percutaneous port, through a stab wound or puncture, through a small incision, for example, in the chest or in the abdomen, or in combinations thereof. It is also contemplated that the mapping instrument 312 may be used in other ways, for example, in open-chest surgery on a heart in which the sternum is split and the rib cage opened with a retractor.

The mapping system 310, and in particular the mapping instrument 312, described above with respect to FIG. 14 is but one acceptable configuration in accordance with the present invention. That is to say, the system 310 and/or the instrument 312 can assume other forms and/or include additional features while still providing a mapping instrument having a shaft that independently maintains varying shapes associated with a straight state and a bent state, and is indifferent to rotational orientation in the straight state.

For example, the mapping instrument 312 can include one or more surgeon-controlled switches. For example, a switch may be incorporated in or on the mapping instrument 312 or any other location easily and quickly accessed by the surgeon for regulation of the mapping instrument 312 by the surgeon. The switch may be, for example, a hand switch, a foot switch, or a voice-activated switch comprising voice-recognition technologies. One or more switches may be incorporated into the grip portion 324 of the mapping instrument 312. A switch incorporated into the grip portion 324 may be a switch, such as a membrane switch, encompassing the entire circumference of the mapping instrument 312, thereby effectively being indifferent to a rotational orientation when the surgeon grasps the handle. That is to say, due to the cross-sectional shape of the switch, the mapping instrument 312 may be rotated to any position relative to a central axis A, and still be conveniently controlled by the surgeon.

Alternatively, a hand switch connected to the mapping instrument 312, but not incorporated into the mapping instrument 312, may be used. For example, a switch designed to be worn by a surgeon, for example on a surgeon's thumb, may be used to activate and/or deactivate the mapping instrument 312. A switch may be incorporated into a cuff or strap that is placed on or around the thumb or finger of a surgeon. Alternatively, a switch may be designed to fit comfortably in a surgeon's palm.

One or more visual and/or audible signals used to alert a surgeon to the completion or resumption of a procedure, for example, may be incorporated into the mapping instrument 312. For example, a beeping tone or flashing light that increases in frequency as the mapping/pacing period ends or begins may be used. Alternatively or in addition, an indicator light otherwise located on the mapping instrument 312 can be inductively coupled to the diagnostic device 316 and adapted such that when power is being delivered to the mapping instrument 312, the light is visible to the surgeon or other users.

Figure 20A:
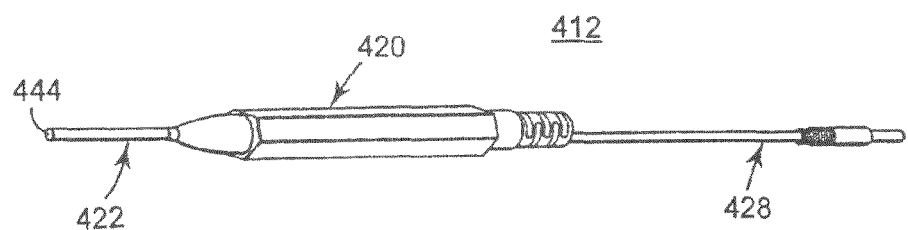
FIGS. 20A and 20B are side perspective views of an alternative embodiment of a mapping instrument in accordance with the present invention.
Figure 20B:
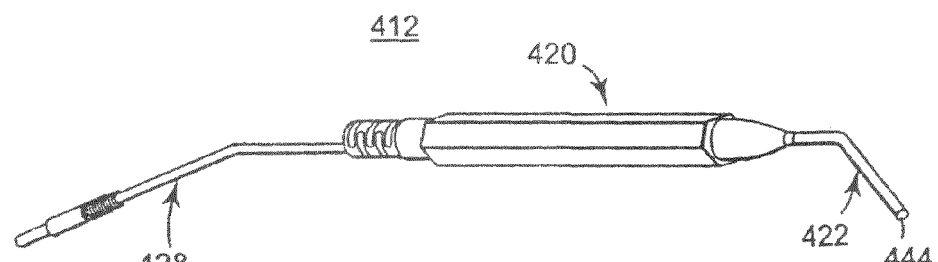

An alternative embodiment, mapping instrument 412 is provided in FIGS. 20A and 20D. The mapping instrument 412 is highly similar to the mapping instrument 312 (FIG. 14) previously described, and includes a handle 420, a shaft 422 and wiring 428. The shaft 422 is virtually identical to the shaft 322 (FIG. 14) previously described, and forms a tip 444. The shaft 422 is adapted to be bendable from a straight state (FIG. 20A) to multiple bent states (one of which is illustrated in FIG. 20B), with die shaft 422 independently maintaining a shape associated with the particular state. Similar to previous embodiments, the wiring 428 electrically couples the diagnostic device 316 (FIG. 14) to the shaft 422.

The handle 420 varies from the handle 320 (FIG. 14) previously described in that the handle 420 does not define a curved outer surface. Instead, the handle 420 is hexagonal in transverse cross-section. This alternative configuration is, however, indifferent to rotational orientation when grasped by a user, thereby promoting the preferred ease of use feature previously described. Notably, the handle 420 can alternatively be formed to a variety of other symmetrical transverse cross-sectional shapes (e.g., octagonal, etc.).

In yet another alternative embodiment, the mapping system 310 (FIG. 14) further includes a controller (not shown) that can also gather and process information from the mapping instrument 312 and/or one or more sensors or sensing elements such as temperature sensors or probes. For example, a temperature sensor coupled to the controller can be located in the distal section 342 (FIG. 14) of the mapping instrument 312. The temperature sensor may be a thermocouple element that measures tissue temperature. Alternatively, the temperature sensor may be, for example, one or more thermisters, temperature-sensing liquid crystals, temperature-sensing chemicals, thermal cameras, and/or infrared (IR) fiber optics.

Figure 21A:
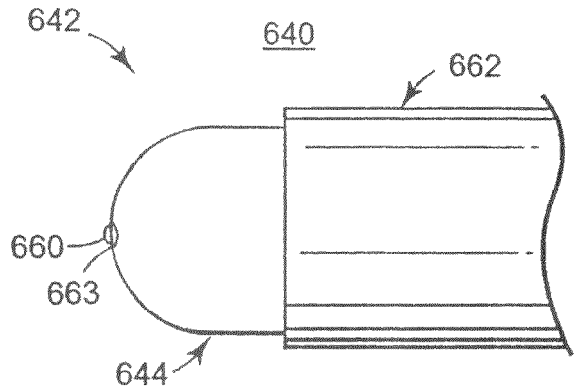
FIG. 21A is an enlarged, perspective view of a distal portion of an alternative embodiment of a mapping instrument in accordance with the present invention.
Figure 21B:
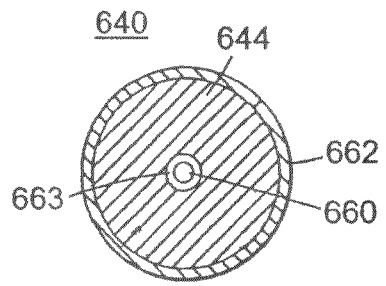
FIG. 21B is an enlarged, transverse, cross-sectional view of the mapping instrument of FIG. 21A.
Figure 21C:
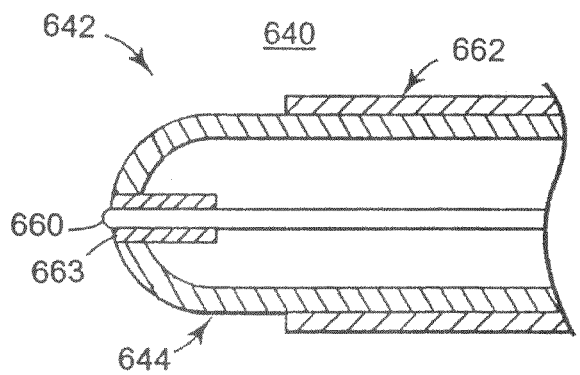
FIG. 21C is an enlarged, longitudinal, cross-sectional view of the mapping instrument of FIG. 21A.

With the above in mind, FIGS. 21A-21C depict a portion of an alternative embodiment mapping device 640, and in particular a distal section 642 thereof. The mapping instrument 640 is highly similar to previous embodiments, and includes a shaft (not shown) terminating at an electrically conductive tip 644. Further, the mapping instrument 640 includes one or more sensors 660, for example, a temperature probe for monitoring tissue temperature. The sensor 660 may be placed at the tip 644. A ring of insulation material 663 may be used to electrically and thermally isolate sensor 660 from the electrically conductive tip 644. The preferred central placement of the sensor 660 at the tip 644 allows the sensor 660 to directly contact a tissue surface in a number of orientations. An alternative embodiment sensor 660 may include an IR optical fiber system, for example, to monitor temperature based on IR. The sensor 660 may be positioned adjacent tip 644 (not shown) or within tip 644 (FIGS. 21A-21C).

Sensing elements 660 can be coupled to visual and/or audible signals used to alert a surgeon to a variety of procedural conditions. For example, a beeping tone or flashing light that increases in frequency as temperature of the tissue exceeds a predetermined amount can be used.

In one embodiment, diagnostic device 316 can incorporate one or more switches to facilitate regulation of various components of mapping system 310 (FIG. 14) by the surgeon. One example of such a switch is a foot pedal. The switch can also be, for example, a hand switch as described above, or a voice-activated switch comprising voice-recognition technologies. The switch can be incorporated in or on one of the surgeon's instruments, such as surgical site retractor, e.g., a sternal or rib retractor, or the mapping instrument 312 (FIG. 14), or any other location easily and quickly accessed by the surgeon. The diagnostic device 316 can also include a display or other means of indicating the status of various components to the surgeon, such as a numerical display, gauges; a monitor display or audio feedback.

Finally, a visual and/or audible signal used to alert a surgeon to the completion or resumption of sensing, monitoring, pacing and/or mapping can be incorporated into the controller. For example, a beeping tone or flashing light that increases in frequency as the pacing period ends or begins can be provided.

In yet another embodiment, and with general reference to FIG. 14, the mapping instrument 312 and/or the diagnostic device 316 can be slaved to a robotic system or a robotic system may be slaved to the mapping instrument 312 and/or the diagnostic device 316.

The handle and shaft of the mapping instrument of the present invention are configured to be indifferent to rotational orientation when initially presented to a surgeon. Subsequently, the surgeon can conveniently shape or bend the shaft so as to provide a shape most conducive to assessing the lesion pattern required by the particular surgical procedure. In this regard, the shaft independently maintains the selected shape throughout the particular mapping/pacing procedure. Subsequently, the shaft can be re-shaped back to a straight configuration, or to any other desired curvature.

Figure 19B:
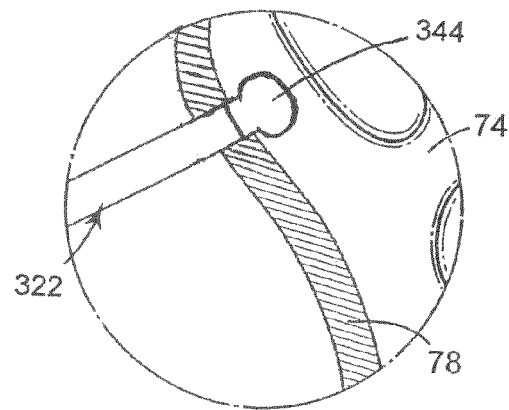
FIG. 19B is an enlarged illustration of a portion of FIG. 19A.

In one embodiment, mapping instrument 312 may be used to pace the heart. For example, mapping instrument 312 may be connected to an external temporary pacemaker, e.g., the Medtronic External Temporary Pacemaker model 5388 or the Medtronic 2090/2290 Programmer/Analyzer. Mapping instrument 312 may be used to temporarily pace atrial tissue of the heart and/or ventricular tissue of the heart. For pacing the heart, tip 344 of mapping instrument 312 is put into contact with tissue to be paced. For example, in one embodiment, a textured ball tip electrode 344 is placed into contact with atrial tissue (FIGS. 19A and 19B).

In one embodiment, a pacing threshold for the mapping instrument 312 for pacing atrial tissue is < 10 mA @ 0.5 ms using the Medtronic 5388 pacemaker. Medtronic's 5388 pacemaker has a maximum output of 20 mA. Ablation lesion testing may be performed by finding the pacing threshold outside the isolated tissue area 74 and then placing the device inside the isolated tissue area 74, as shown in FIGS. 19A and 19B, with 2× the pacing threshold of the non-isolated area. A pacing threshold of 10 mA or less allows the mapping instrument 312 to be used for typical lesion testing after cardiac ablation of atrial tissue 78. Since the Medtronic 5388 device is a current controlled device, pacing threshold for the 5388 temporary pacemaker is the minimum current at which the temporary pacemaker continuously controls pacing of the heart.

The pacing threshold for the mapping instrument 312 for pacing ventricle tissue is < 5V @ 0.5 ms using Medtronic's 2090/2290 Programmer/Analyzer and the resistance at 5V preferably is > 500Ω (5V/500Ω=10 mA). Pacing threshold for the Programmer/Analyzer is the lowest voltage at which continuous capture of the heart occurs. Mapping instrument 312 is used in a unipolar mode (measuring between the tip 344 and a grounding electrode 318, for example a grounding needle placed, for example, in the extrathoracic tissue). Pacing resistance can be measured at 5V while using the Programmer/Analyzer to measure pacing thresholds.

In one embodiment, the mapping instrument 312 can be used in left sided epicardial lead placement procedures. During these procedures, epicardial mapping is useful in identifying the optimal site for epicardial lead placement on the left ventricle. In one embodiment, the mapping instrument 312 is used to pace one or more ventricles and the synchronicity of left ventricular contraction is evaluated, for example, with TEE. Alternatively, tissue Doppler ultrasound may be used to measure contraction patterns and to locate the site where, biventricular pacing could result in the most effective contraction of the left ventricle. While Doppler ultrasound may be may be more effective than TEE, it is not commonly available and may require the patient's chest to be closed in order to provide useful data.

Figure 22:
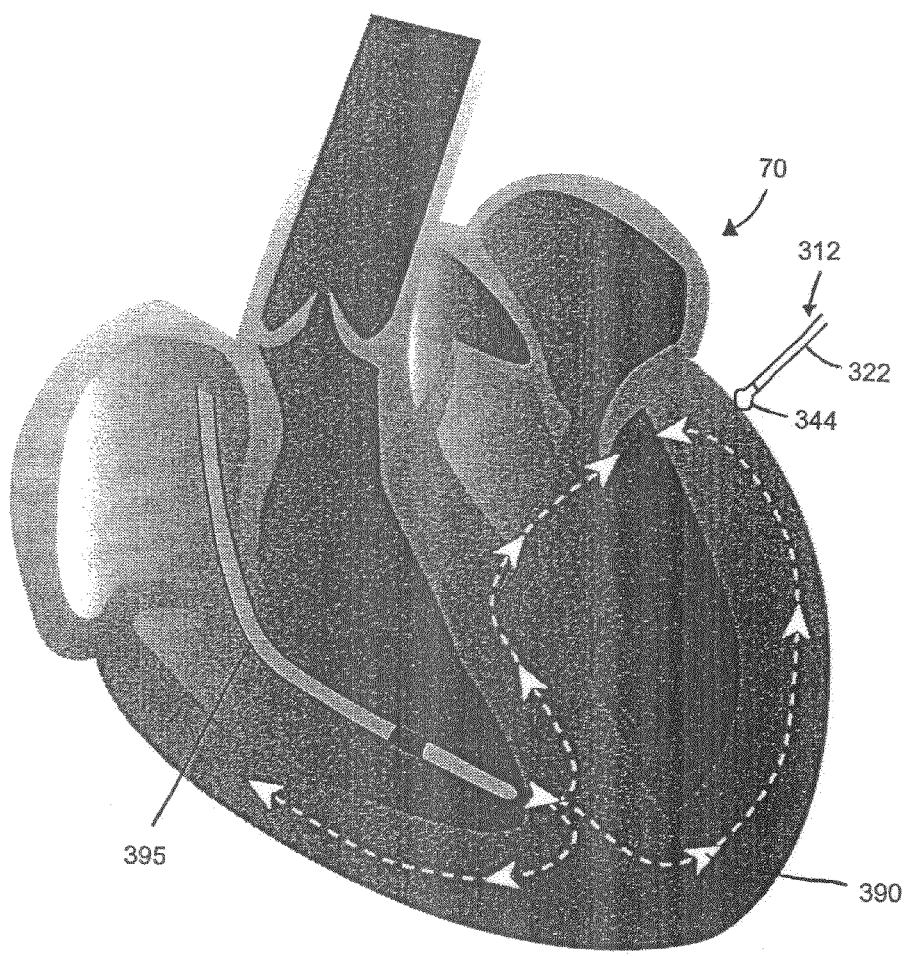
FIG. 22 is a cut-away illustration of a patient's heart depicting activation patterns and cell-to-cell conduction from right ventricular pacing.

Another approach entails identifying the site of latest left ventricular, electrical activity following a paced right ventricular beat. This electrical site may correlate with the site of latest mechanical activity. Pacing at the site of latest activation can create two contraction wavefronts from electrically opposite sides of the heart while accommodating any unusual conduction pathways. Theoretically, this will create collision of the right and left ventricular wavefronts equidistant from the electrodes on both sides of the ventricle thereby minimizing dysynchrony. The hypothesis for this activation sequence was originally described more than 20 years ago. FIG. 22 illustrates activation patterns 390 and cell-to-cell conduction from right ventricular pacing by an electrode 395 placed in the right ventricle.

The approach of identifying the site of latest left ventricular electrical activity determines the time between a paced event in the right ventricle and the corresponding sensed event in the left ventricle. As the heart is paced in the right ventricle, the electrode tip 344 of mapping instrument 312 is placed into contact of epicardial tissue of the left ventricle and the time at which a depolarization wave is sensed over the left ventricle is noted.

Figure 23:
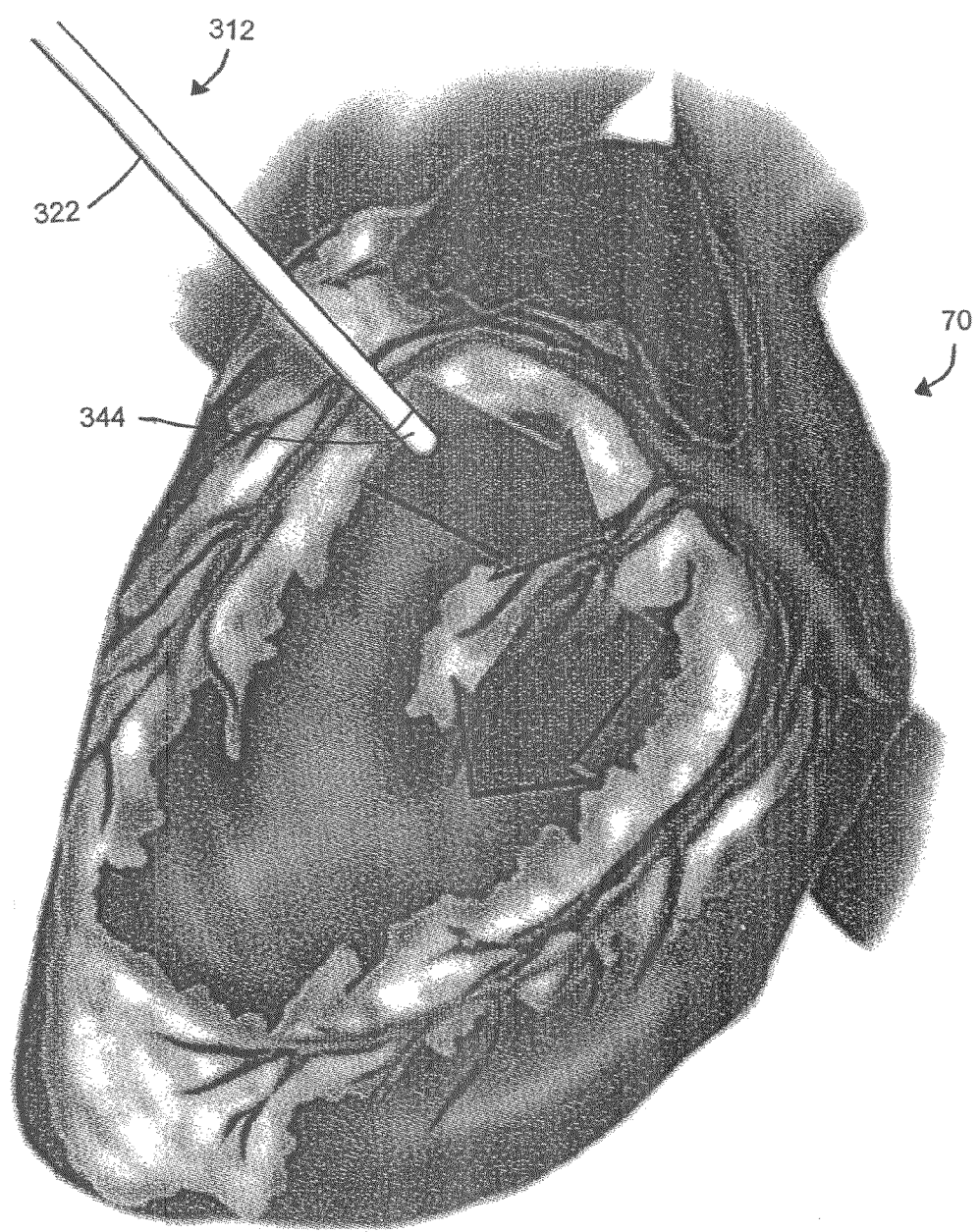
FIG. 23 is an illustration of a patient's heart depicting epicardial mapping to optimize left ventricular lead placement.

This timeframe is called the "paced depolarization interval" (PDI). Starting at a posterior lateral position, approximately six sites should be measured, see FIG. 23. The longest time interval or maximum PDI is the point that is electrically farthest from the right ventricular electrode and is generally the site for optimal lead placement.

Paced depolarization intervals will vary among patients. PDI values of normal hearts are usually 100 ms or less, but patients who have congestive heart failure and larger hearts typically have values between 150 ms and 200 ms. In general, the larger the heart, the larger the PDI. In addition, PDIs below 150 ms tend to indicate the lead location is not optimal.

When measuring paced depolarization intervals, it is very important to use a paced beat rather than an intrinsic beat. A CRT system will pace both ventricles and the lead placement site should be chosen in accordance with the way the CRT system functions. Pacing of the right ventricle can be accomplished using either an implanted pacemaker or a programmer/analyzer, for example, the Medtronic 2090/2290 Programmer/Analyzer.

If the patient already has an implanted pacemaker, it is not necessary to remove it or externalize the right ventricular lead prior to mapping for left ventricular lead placement. The pacemaker should be programmed to pace the right ventricle continuously in the unipolar mode. A V pacing pulse may be used to help visualization of the pacing spike on the mapping electrode signal. Mapping instrument 312 should be connected to the programmer or other device to display electrograms (EGMs), which should either be frozen electronically in the programmer or printed on paper for manual measurement. From the EGM, the pacing spike should be seen, as should the depolarization wavefront that passes under the pacing ventricular mapping electrode. The time between the pacing spike and the depolarization wave on the EGM signal is the PDI. Maximizing the PDI may optimize cardiac resynchronization.

Figure 24:
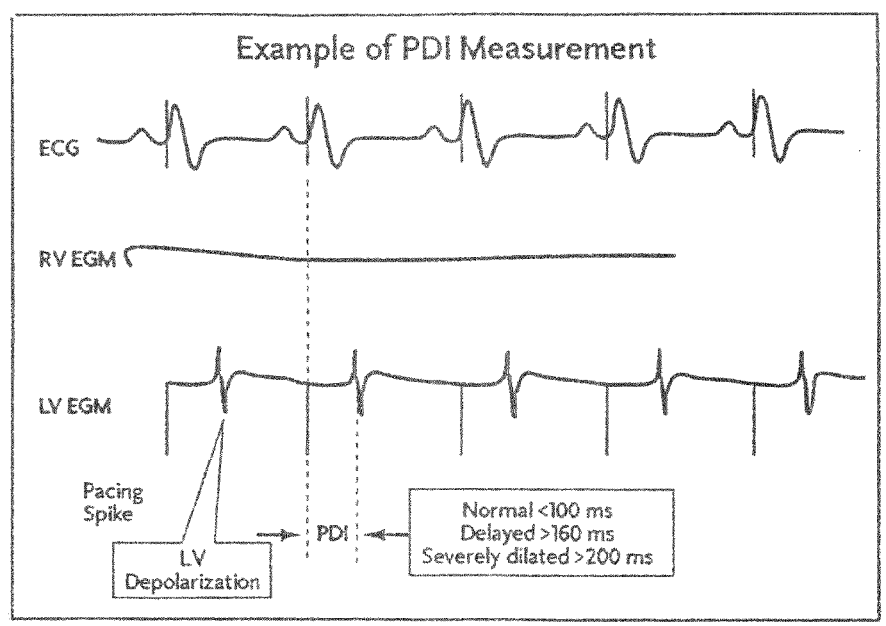
FIG. 24 is a schematic of PDI measurement in accordance with one embodiment of the present invention.

A Programmer/Analyzer, for example, the Medtronic 2090/2290 Programmer/Analyzer, may be used to measure the maximum PDI. If a right ventricular lead is not accessible, the mapping electrode can be connected to either the atrial or ventricular channel of the analyzer. The pacing spike and the depolarization wavefront should both be visible on the data strip, see FIG. 24. During this measurement, the right ventricular lead should be pacing the heart with the implanted pacemaker in the unipolar mode. The time can then be measured between the pacing spike and the left ventricular deflection.

Figure 25:
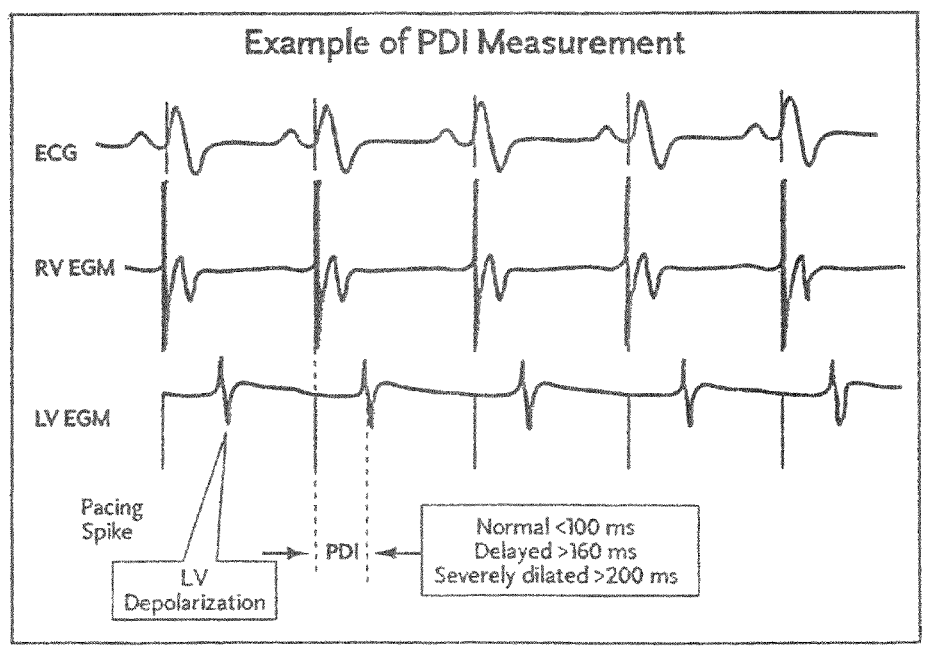
FIG. 25 is a schematic of PDI measurement in accordance with one embodiment of the present invention.

If the right ventricular lead is accessible, both leads can be connected to the analyzer. The right ventricular lead is connected to the ventricular channel and the mapping instrument 312 is connected to the atrial channel. The analyzer can then pace the right ventricular lead, sense the left ventricular mapping electrode, and display the time between the paced and sensed events on the screen. In this case, the right ventricular (RV) and left ventricular (LV) EGMs shown in FIG. 25 will both be visible. The strips can be frozen electronically in the analyzer and the maximum EDI measured with calipers, or they can be printed on paper for manual measurement.

In another embodiment, the electrosurgical instrument 12 includes a mode switch (not shown). For example, a surgeon-controlled mode switch may be incorporated in or on the electrosurgical instrument 12 or any other location easily and quickly accessed by a surgeon for switching between an ablation mode, a mapping mode and/or a pacing mode. The switch may be, for example, a hand switch, a foot switch, or a voice-activated switch comprising voice-recognition technologies. A mode switch would allow the electrosurgical instrument 12 to be used as both an ablation tool and a mapping/pacing tool. For example, an energy source may be electrically connected to electrosurgical instrument 12, wherein the energy source comprises ablation energy for creating tissue lesions and stimulation energy for pacing the heart. A switch coupled to the energy source may be configured to control delivery of ablation energy and stimulation energy from the energy source to electrosurgical instrument 12. The delivery of ablation energy to electrosurgical instrument 12 may be stopped when the delivery of stimulation energy to electrosurgical instrument 12 is started and the delivery of stimulation energy to electrosurgical instrument 12 may be stopped when the delivery of ablation energy to electrosurgical instrument 12 is started. The switch may also be coupled to a source of conductive fluid. In this case, the switch may be configured to control delivery of fluid from a source of conductive fluid to the internal lumen of the instrument. For example, the delivery of fluid to the internal lumen of the instrument may be stopped when the delivery of ablation energy to the tip of the instrument is stopped and the delivery of fluid to the internal lumen of the instrument may be started when the delivery of ablation energy to the tip of the instrument is started.

In yet another alternative embodiment, the electrosurgical instrument 12 includes a visual and/or audible signaling device (not shown) used to alert a surgeon to any change in the mode of the device. For example, a beeping tone or flashing light can be used to alert the surgeon that the electrosurgical instrument 12 is in an ablation mode or has changed from a mapping/pacing mode to an ablation mode. For example, one or more indicator lights located on the instrument can indicate the delivery of ablation energy and/or stimulation energy for pacing heart tissue.

Although the invention has been described above in connection with particular embodiments and examples, it will be appreciated by those skilled in the art that the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

What is claimed is:

1. A method of performing an ablation procedure, the method comprising:

providing a first instrument including an elongated shaft and a handle, the shaft defining a proximal section rigidly coupled to the handle, a distal section forming an electrically conductive tip;

positioning the tip of the first instrument through a patient's chest;

applying ablation energy to the tip of the first instrument while contacting cardiac tissue;

creating an ablation lesion to isolate an area of cardiac tissue;

providing a second instrument including an elongated shaft and a handle, the shaft defining a proximal section rigidly coupled to the handle, a distal section forming an electrically conductive tip;

positioning the tip of the second instrument through a patient's chest; and applying stimulation energy to the tip of the second instrument while contacting the area of isolated cardiac tissue to assess transmurality of the ablation lesion.

2. The method of claim 1, wherein the first instrument further comprises an internal lumen extending from the proximal section of the shaft and in fluid communication with at least one passage formed in the distal section of the shaft.

3. The method of claim 2, further comprising:

dispensing conductive fluid from the internal lumen of the shaft via the at least one passage.

4. The method of claim 1, wherein the ablation energy is radiofrequency energy.

5. The method of claim 1, wherein the step of applying ablation energy to the tip of the first instrument includes dragging the tip of the first instrument along the cardiac tissue.

6. A method of performing an ablation procedure, the method comprising:

providing an instrument including an elongated shaft and a handle, the shaft defining a proximal section rigidly coupled to the handle, a distal section forming an electrically conductive tip;

positioning the tip through a patient's chest;

applying ablation energy to the tip while contacting cardiac tissue;

creating an ablation lesion to isolate an area of cardiac tissue;

stopping the application of ablation energy to the tip;

repositioning the tip; and applying stimulation energy to the tip while contacting the area of isolated cardiac tissue to assess transmurality of the ablation lesion.

7. The method of claim 6, wherein the instrument further comprises an internal lumen extending from the proximal section of the shaft and in fluid communication with at least one passage formed in the distal section of the shaft.

8. The method of claim 7, further comprising:

dispensing conductive fluid from the internal lumen of the shaft via the at least one passage while applying ablation energy to the tip.

9. The method of claim 6, wherein the ablation energy is radio frequency energy.

10. The method of claim 6, wherein the step of repositioning the tip includes contacting the tip against tissue entirely within the area of isolated tissue, and the step of applying stimulation energy to the tip occurs after the step of repositioning the tip.

11. A method of performing an ablation procedure, the method comprising:

providing an instrument including an elongated shaft and a handle, the shaft defining a proximal section rigidly coupled to the handle, a distal section forming an electrically conductive tip;

advancing the tip of the instrument through a patient's chest and into the patient's coronary sinus;

positioning the tip of the instrument in the patient's coronary sinus between an existing lesion encircling at least a portion of the patient's pulmonary veins and the annulus of the patient's mitral valve;

applying ablation energy to the tip of the instrument while the tip is positioned in the coronary sinus; and creating an ablation lesion in an area of cardiac tissue surrounding the tip.

* * * * *